(12) United States Patent
DiMauro et al.

(10) Patent No.: US 8,361,467 B2
(45) Date of Patent: Jan. 29, 2013

(54) TRANS-CAPSULAR ADMINISTRATION OF HIGH SPECIFICITY CYTOKINE INHIBITORS INTO ORTHOPEDIC JOINTS

(75) Inventors: Thomas M. DiMauro, Southboro, MA (US); Mohamed Attawia, Canton, MA (US); Hassan Serhan, South Easton, MA (US); Martin A. Reynolds, Mansfield, MA (US); Melissa Grace, Raynham, MA (US); Sudhakar Kadiyala, South Easton, MA (US); David Urbahns, Barrington, RI (US); Scott Bruder, Sudbury, MA (US); Gregory Collins, East Sandwich, MA (US); Laura J. Brown, Hamilton Square, NJ (US); Jeff Geesin, Doylestown, PA (US); Pamela L. Plouhar, South Bend, IN (US); Catherine Smith, East Falmouth, MA (US); John Siekierka, Towaco, NJ (US)

(73) Assignee: DePuy Spine, Inc., Raynham, MA (US)

( * ) Notice: Subject to any disclaimer, the term of this patent is extended or adjusted under 35 U.S.C. 154(b) by 514 days.

(21) Appl. No.: 10/630,227

(22) Filed: Jul. 30, 2003

(65) Prior Publication Data

US 2005/0025765 A1 Feb. 3, 2005

(51) Int. Cl.
*A61K 39/395* (2006.01)
*A61K 39/00* (2006.01)
*A61K 38/18* (2006.01)

(52) U.S. Cl. ............... 424/141.1; 424/133.1; 424/142.1; 424/156.1; 424/158.1; 514/7.6; 514/8.2; 514/8.8

(58) Field of Classification Search .................. None
See application file for complete search history.

(56) References Cited

U.S. PATENT DOCUMENTS

| | | |
|---|---|---|
| 3,678,158 A | 7/1972 | Sussman |
| 4,341,867 A | 7/1982 | Johansen |
| 4,427,649 A | 1/1984 | Dingle et al. |
| 4,435,506 A | 3/1984 | Jackson et al. |
| 4,696,816 A | 9/1987 | Brown |
| 5,095,037 A | 3/1992 | Iwamitsu et al. |
| 5,116,964 A | 5/1992 | Capon et al. |
| 5,194,596 A * | 3/1993 | Tischer et al. ............... 530/399 |
| 5,223,248 A | 6/1993 | McNamara et al. |
| 5,225,538 A | 7/1993 | Capon et al. |
| 5,231,024 A | 7/1993 | Moeller et al. |
| 5,258,371 A | 11/1993 | Golub et al. |
| 5,270,300 A | 12/1993 | Hunziker |
| 5,368,841 A | 11/1994 | Trauner et al. |
| 5,447,851 A | 9/1995 | Beutler et al. |
| 5,510,370 A | 4/1996 | Hock |
| 5,602,156 A | 2/1997 | Kohn et al. |
| 5,656,272 A | 8/1997 | Le et al. |
| 5,656,644 A | 8/1997 | Adams et al. |
| 5,728,396 A | 3/1998 | Peery et al. |
| 5,833,984 A | 11/1998 | Eibl et al. |
| 5,842,477 A | 12/1998 | Naughton et al. |
| 5,942,499 A | 8/1999 | Radomsky |
| 5,965,583 A | 10/1999 | Beers et al. |
| 6,049,026 A | 4/2000 | Muschler |
| 6,277,969 B1 | 8/2001 | Le et al. |
| 6,284,471 B1 | 9/2001 | Le et al. |
| 6,294,170 B1 | 9/2001 | Boone et al. |
| 6,300,347 B1 | 10/2001 | Révész |
| 6,340,369 B1 | 1/2002 | Ferree |
| 6,352,557 B1 | 3/2002 | Ferree |
| 6,419,944 B2 | 7/2002 | Tobinick |
| 6,541,477 B2 | 4/2003 | Goehring et al. |
| 6,554,830 B1 | 4/2003 | Chappius |
| 6,590,081 B1 | 7/2003 | Zhang |
| 6,593,310 B1 | 7/2003 | Cullis-Hill |
| 6,623,472 B1 | 9/2003 | Reinecke et al. |
| 6,713,246 B1 | 3/2004 | Reinecke et al. |
| 6,756,215 B1 * | 6/2004 | Wolfraim et al. ............ 435/69.1 |
| 7,097,834 B1 * | 8/2006 | Boyle ........................ 424/130.1 |
| 7,344,716 B2 | 3/2008 | DiMauro et al. |
| 7,429,378 B2 | 9/2008 | Serhan et al. |
| 7,553,827 B2 | 6/2009 | Attawia et al. |
| 2001/0006948 A1 | 7/2001 | Kang et al. |
| 2001/0016195 A1 | 8/2001 | Tobinick |

(Continued)

FOREIGN PATENT DOCUMENTS

AU  2003/263340 A1  3/2004
EP    0 218 868 A2  4/1987

(Continued)

OTHER PUBLICATIONS

La Van et al. 2003. Nature, Biotechnology. 21:1184-1191.*
Lehman et al. 2002. J Pediatrics. 140:125-7.*
http://arthritis.com/od/kneetreatments/g/viscosupplement_p.htm, Dec. 9, 2005.*
Molloy et al. 2003. Sports Med. 33:381-394.*
Cardone et al. 2003. Family Medicine 67:2147-2152.*
www.medicinenet.com, downloaded Jun. 20, 2006.*

(Continued)

*Primary Examiner* — Shulamith H Shafer
(74) *Attorney, Agent, or Firm* — Hamilton, Brook, Smith & Reynolds, P.C.

(57) ABSTRACT

The present invention relates to trans-capsularly administering into a diseased joint a high specificity antagonist selected from the group consisting of:
  i) an inhibitor of a pro-inflammatory interleukin;
  ii) an inhibitor of TNF-α synthesis;
  iii) an inhibitor of membrane-bound TNF-α;
  iv) an inhibitor of a natural receptor of TNF-α;
  v) an inhibitor of NO synthase,
  vi) an inhibitor of $PLA_2$ enzyme;
  vii) an anti-proliferative agent;
  viii) an anti-oxidant;
  ix) an apoptosis inhibitor selected from the group consisting of EPO mimetic peptides, EPO mimetibodies, IGF-I, IGF-II, and caspase inhibitors, and
  x) an inhibitor of MMPs; and
  xi) an inhibitor of p38 kinase.

42 Claims, No Drawings

U.S. PATENT DOCUMENTS

| | | | |
|---|---|---|---|
| 2001/0026801 A1 | 10/2001 | Tobinick | |
| 2002/0010471 A1 | 1/2002 | Wironen et al. | |
| 2002/0026244 A1 | 2/2002 | Trieu | |
| 2002/0032155 A1 | 3/2002 | Ferree | |
| 2002/0082697 A1 | 6/2002 | Damien | |
| 2002/0107200 A1 | 8/2002 | Chang et al. | |
| 2002/0169162 A1* | 11/2002 | Smith et al. | 514/248 |
| 2002/0198599 A1 | 12/2002 | Haldimann | |
| 2003/0007972 A1 | 1/2003 | Tobinick | |
| 2003/0008817 A1* | 1/2003 | Sander et al. | 514/12 |
| 2003/0039651 A1 | 2/2003 | Olmarker | |
| 2003/0049256 A1 | 3/2003 | Tobinick | |
| 2003/0069639 A1 | 4/2003 | Sander et al. | |
| 2003/0134792 A1* | 7/2003 | Pike et al. | 514/12 |
| 2003/0207827 A1 | 11/2003 | Boyle et al. | |
| 2003/0220692 A1 | 11/2003 | Shapiro et al. | |
| 2003/0235585 A1* | 12/2003 | Fischkoff et al. | 424/145.1 |
| 2004/0022864 A1 | 2/2004 | Freyman et al. | |
| 2004/0126372 A1 | 7/2004 | Banerjee et al. | |
| 2004/0193274 A1 | 9/2004 | Trieu | |
| 2004/0229786 A1 | 11/2004 | Attawia et al. | |
| 2004/0229878 A1 | 11/2004 | DiMauro et al. | |
| 2005/0038001 A1 | 2/2005 | Attawia et al. | |
| 2005/0054595 A1 | 3/2005 | Binette et al. | |
| 2005/0100538 A1 | 5/2005 | Mohamed et al. | |
| 2005/0112091 A1 | 5/2005 | DiMauro et al. | |
| 2005/0208095 A1 | 9/2005 | Hunter et al. | |
| 2005/0282783 A1 | 12/2005 | Bujoli et al. | |
| 2007/0269413 A1 | 11/2007 | Serhan et al. | |
| 2008/0213261 A1 | 9/2008 | DiMauro et al. | |
| 2009/0068270 A1 | 3/2009 | Attawia et al. | |
| 2009/0155364 A1 | 6/2009 | Serhan et al. | |
| 2009/0162351 A1 | 6/2009 | Brown et al. | |
| 2009/0162376 A1 | 6/2009 | Brown et al. | |
| 2009/0175943 A1 | 7/2009 | Attawia et al. | |
| 2009/0324558 A1 | 12/2009 | Attawia et al. | |

FOREIGN PATENT DOCUMENTS

| | | |
|---|---|---|
| EP | 0 288 088 B1 | 10/1988 |
| EP | 0 438 234 A1 | 7/1991 |
| EP | 0 950 417 A2 | 10/1999 |
| EP | 1 133 995 A2 | 9/2001 |
| EP | 1 153 607 * | 11/2001 |
| EP | 1 153607 A2 | 11/2001 |
| EP | 1153607 A2 | 11/2001 |
| EP | 1 464 307 A1 | 10/2004 |
| WO | WO 91/02078 | 2/1991 |
| WO | WO 92/07076 | 4/1992 |
| WO | WO 92/16553 | 10/1992 |
| WO | WO 93/16099 A2 | 8/1993 |
| WO | WO 97/28828 | 8/1997 |
| WO | WO 98/24477 | 6/1998 |
| WO | WO 99/45923 A1 | 9/1999 |
| WO | WO 00/18409 A1 | 4/2000 |
| WO | WO 00/50079 A1 | 8/2000 |
| WO | WO 01/85179 A2 | 11/2001 |
| WO | WO 02/057240 A1 | 7/2002 |
| WO | WO 02/100387 A1 | 12/2002 |
| WO | WO 03/000190 A2 | 1/2003 |
| WO | WO 2004/022078 A1 | 3/2004 |
| WO | WO 2005/000283 A2 | 1/2005 |
| WO | WO 2005/011689 A2 | 2/2005 |
| WO | WO 2005/049055 A1 | 6/2005 |
| WO | WO 2005/053795 A2 | 6/2005 |
| WO | WO 2005/110276 A1 | 11/2005 |
| WO | WO 2006/031376 A2 | 3/2006 |

OTHER PUBLICATIONS

Sampaio et al. 1991. J. Exp. Med. 173:699-703.*
Mullet et al. 1999. Biorganic and Medicinal Chem Lett. 9:1625.*
Teo SK. 2005. AAPS Journal. 7:Article3.*
Moreira et al. 1993. J. Exp Med. 177:1675-1680.*
Braun et al. 2003. Expert Opin Biol. Ther. 3:141-168.*
Benjamin et al. 1998 Development 125:1591-1598.*
Vukicevic et al. 1996. PNAS 93:9021-9026.*
Brekke et al. Nature Reviews, Drug Discovery 2003. 2:52-62.*
Rheumatoid Arthritis, MedicineNet.com http://www.medicinenet.com/script/main/art.asp?articlekey=466&pf=3&page=1, downloaded Apr. 22, 2011.*
Weinblatt et al. 2003. Arthritis and Rheumatism 48:35-45.*
van Beuningen et al. 1998. Osteoarthritis and Cartilage 6:306-317.*
Braun, J. and Sieper J., "Overview of the Use of the Anti-TNF Agent Infliximab in Chronic Inflammatory Diseases," Expert Opin. Biol. Ther. 3(1):141-168 (2003).
Braun, J., et al., "Anti-Tumour Necrosis Factor α Therapy for Ankylosing Spondylitis: International Experience," Ann. Rheum. Dis., 61(Supp. III):iii51-iii60 (2002).
Olmarker, K. and Rydevik, B., "Selective Inhibition of Tumor Necrosis Factor-α Prevents Nucleus Pulposus-Induced Thrombus Formation, Intraneural Edema, and Reduction of Nerve Conduction Velocity," Spine, 26(8):863-869 (2001).
Aoki, Y., et al., "Local Application of Disc-Related Cytokines on Spinal Nerve Roots," Spine 27(15): 1614-1617 (2002).
Tobinick, E.L. and Britschgi-Davoodifar, S., "Perispinal TNF-Alpha Inhibition for Discogenic Pain," Swiss Med. Weekly, 133:170-77 (2003).
Maeda, S. and Kokubun, S., "Changes With Age in Proteoglycan Synthesis in Cells Cultured In Vitro From the Inner and Outer Rabbit Annulus Fibrosus," Spine, 25(2):166-169 (2000).
Igarashi et al., Inflammatory Cytokines From Facet Joint Tissue in Degenerative Lumbar Disorder, ISSLS Abstract #262 (May 13-17, 2003).
Wittenberg, et al., "In Vitro Release of Prostaglandins and Leukotrienes From Synovial Tissue, Cartilage, and Bone in Degenerative Joint Diseases," Arthritis Rheum., 36(10):1444-1450 (Oct. 1993).
Kawakami, M. et al., "Possible Mechanism of Painful Radiculopathy in Lumbar Disc Herniation," Clin. Orthop. 351:241-251(1998).
Gordon, J.L., et al., "Metalloproteinase Inhibitors as Therapeutics," Clin. Exp. Rheumatol., 11(Supp 8): S91-S94 (1993).
Johnson, W.H., et al., "Collagenase Inhibitors: Their Design and Potential Therapeutic Use," J. Enzyme Inhib., 2:1-22 (1987).
Möller, A. et al., "Monoclonal Antibodies to Human Tumor Necrosis Factor α: In Vitro and In Vivo Application," Cytokine 2(3):162-169 (1990).
Liang, C.-M., et al., "Production and Characterization of Monoclonal Antibodies Against Recombinant Human Tumor Necrosis Factor/Cachectin," Biochem. Biophys. Res. Comm. 137:847-854 (1986).
Meager, A., et al., "Preparation and Characterization of Monoclonal Antibodies Directed Against Antigenic Determinants of Recombinant Human Tumour Necrosis Factor (rTNF)," Hybridoma 6(3):305-311 (1987).
Fendly et al., "Murine Monoclonal Antibodies Defining Neutralizing Epitopes on Tumor Necrosis Factor," Hybridoma 6:359-370 (1987).
Bringman, T.S., et al., "Monoclonal Antibodies to Human Tumor Necrosis Factors Alpha and Beta: Application for Affinity Purification, Immunoassays, and as Structural Probes," Hybridoma 6(5):489-507 (1987).
Hirai, M., et al., "Production and Characterization of Monoclonal Antibodies to Human Tumor Necrosis Factor," J. Immunol. Meth. 96:57-62 (1987).
Schall, T., et al., "Molecular Cloning and Expression of a Receptor for Human Tumor Necrosis Factor," Cell, 61:361-370 (1990).
Loetscher, H., et al., "Molecular Cloning and Expression of the Human 55 kd Tumor Necrosis Factor Receptor," Cell, 61:351-359 (1990).
Corcoran, A., et al., "Characterization of Ligand Binding by the Human p55 Tumour-Necrosis-Factor Receptor," Eur. J. Biochem., 223:831-840 (1994).
Engelmann, H. et al., "Two Tumor Necrosis Factor-Binding Proteins Purified From Human Urine," J. Biol. Chem., 265(3):1531-1536 (1990).
Lesslauer, W., et al., "Recombinant Soluble Tumor Necrosis Factor Receptor Proteins Protect Mice from Lipopolysaccharide-Induced Lethality," Eur. J. Immunol., 21:2883-2886 (1991).
Ashkenazi, A., et al., "Protection Against Endotoxic Shock by a Tumor Necrosis Factor Receptor Immunoadhesin," Proc. Natl. Acad. Sci. USA 88:10535-10539 (1991).

Peppel, K., et al., "A Tumor Necrosis Factor (TNF) Receptor-IgG Heavy Chain Chimeric Protein as a Bivalent Antagonist of TNF Activity," *J. Exp. Med.*, 174:1483-1489 (1991).

Capon, D., et al., "Designing CD4 Immunoadhesins for AIDS Therapy," *Nature*, 337:525-531 (1989).

Kolls, J., et al., "Prolonged and Effective Blockade of Tumor Necrosis Factor Activity Through Adenovirus-Mediated Gene Transfer," *Proc. Natl. Acad. Sci. USA* 91:215-219 (1994).

Butler, D., et al., "TNF Receptor Fusion Proteins are Effective Inhibitors of TNF-Mediated Cytotoxicity on Human KYM-1D4 Rhabdomyosarcoma Cells," *Cytokine*, 6(6):616-623 (1994).

Baker, D., et al., "Control of Established Experimental Allergic Encephalomyelitis by Inhibition of Tumor Necrosis Factor (TNF) Activity within the Central Nervous System using Monoclonal Antibodies and TNF Receptor-Immunoglobulin Fusion Proteins," *Eur. J. Immunol.*, 24:2040-2048 (1994).

Zhang, C., et al., "Mitogen-activated Protein (MAP) Kinase Regulates Production of Tumor Necrosis Factor-α and Release of Arachidonic Acid in Mast Cells," *J. Biol. Chem.*, 272(20): 13397-13402 (1997).

Pargellis, C., et al., "Inhibition of p38 MAP Kinase by Utilizing a Novel Allosteric Binding Site," *Nature Structural Biology*, 9(4): 268-272 (2002).

Chae, H.J., et al., "The p38 Mitogen-activated Protein Kinase Pathway Regulates Interleukin-6 Synthesis in Response to Tumor Necrosis Factor in Osteoblasts," *Bone*, 28(1): 45-53 (2001).

Cirillo, P., et al., "The Non-Diaryl Heterocycle Classes of p38 MAP Kinase Inhibitors," *Current Topics in Medicinal Chemistry*, 2:1021-1035 (2002).

Boehm, J. and Adams, J., "New Inhibitors of p38 Kinase," *Exp. Opin, Ther. Patents*, 10(1):25-38 (2000).

Lee et al., "Inhibition of p38 MAP Kinase as a Therapeutic Strategy," *Immunopharmacology*, 47:185-2001 (2000).

Brown, K., et al., "Gelatin/Chondroitin 6-Sulfate Microspheres for the Delivery of Therapeutic Proteins to the Joint," *Arthritis. Rheum.*, 41(12):2185-2195 (1998).

Burke, J.G., et al., "Intervertebral Discs Which Cause Low Back Pain Secrete High Levels of Proinflammatory Mediators," *JBJS*, 84-B(2):196-201 (2002).

Gabay, C., "IL-1 Trap," *Curr. Opin. Invest. Drugs, Curr. Drugs*, London, GB, 4(5):593-597 (2003).

Dayer, J.M., "The Pivotal Role of Interleukin-1 in the Clinical Manifestations of Rheumatoid Arthritis," *Rheumatology*, Oxford Univeristy Press, London, GB, 42(Suppl 2):ii03-ii10 (2003).

Abstracts of the North American Spine Society 17 Annual Meeting, Montreal, Canada, Oct. 29 through Nov. 2, 2002, *The Spine Journal* 2(5 Suppl):49S-50S (2002).

Ahn, N. U., et al., "Effect of Nutrient Concentration and OP-1 on the Metabolism of Intervertebral Disc: In Vitro Organ Culture Study," 28, Abstracts of the 30th Annual Meeting of the International Society for the Study of the Lumbar Spine, Vancouver, Canada (May 2003).

Alini, M. et al., "A Biological Approach in Treating Disc Degeneration: Not for Today, but Maybe for Tomorrow," *European Spine Journal*, 11(Suppl 2):S215-S220 (2002).

Allali, F. et al., "Increase in Bone Mineral Density of Patients with Spondyloarthropathy Treated with Anti-Tumour Necrosis Factor α," *Ann. Rheum. Dis.*, 62:347-349 (2003).

Andonopoulos, A.P., et al., "Intra-articular Anti-Tumor Necrosis Factor α Antibody in Recalcitrant Arthritis of Behçet's Disease," *Clinical and Experimental Rheumatology* 21(4 Suppl. 30):S57-58 (Jul.-Aug. 2003).

Arai, I., et al., "Pretreatment with Loxoprofen Sodium, 6-OHDA or Anti TNF-Alpha Antibody Reduce Fos-Like Immunoreactivity in Rat Experimental Lumber Disc Herniation," 111, Abstracts of the 30th Annual Meeting of the International Society for the Study of the Lumbar Spine, Vancouver, Canada (May 2003).

Ariga, K. et al., "Mechanical Stress-Induced Apoptosis of Endplate Chondrocytes in Organ-Cultured Mouse Intervertebral Discs," *Spine*, 28(14):1528-1533 (2003).

Biskobing, D.M., "Novel Therapies for Osteoporosis," *Expert Opinion Invest. Drugs*, 12(4):611-621 (2003).

Bokarewa, M., et al., "Local Infusion of Infliximab for the Treatment of Acute Joint Inflammation," *Ann. Rheum Dis* 62: 783-784 (2003).

Burke, J. G., et al., "Human Nucleus Pulposus Secretes Transforming Growth Factor Beta-1 and Basic Fibroblast Growth Factor," 189, Abstracts of the 30th Annual Meeting of the International Society for the Study of the Lumbar Spine, Vancouver, Canada (May 2003).

Cardone, et al., "Diagnostic and Therapeutic Injection of the Hip and Knee," *Family Medicine*, 67:2147-2152 (2003).

Connolly, J., et al., "Development of an Osteogenic Bone-Marrow Preparation," *The Journal of Bone and Joint Surgery, Inc.*, 71-A (5): 684-691 (1989).

Conti, F., et al., "Successful Treatment with Intraarticular Infliximab for Resistant Knee Monarthritis in a Patient with Spondylarthropathy," *Arthritis & Rheumatism* 52(4): 1224-1226 (Apr. 2005).

Cornefjord, M., et al., "Cerebrospinal Fluid Biomarkers in Experimental Spinal Nerve Root Injury," 38, Abstracts of the 30th Annual Meeting of the International Society for the Study of the Lumbar Spine, Vancouver, Canada (May 2003).

Crandall, C., "Combination Treatment of Osteoporosis: A Clinical Review," *J. of Women's Health & Gender-Based Medicine*, 11(3):211-224 (2002).

DeSantis, A. and Buchman, A., "Current and Emerging Therapies in Osteoporosis," *Expert Opin. Pharmacother.*, 3(7):835-843 (2002).

Diwan, A. et al., "Current Concepts in Intervertebral Disk Restoration," *Tissue Engineering in Orthopedic Surgery*, 31(3):453-464 (2000).

Edwards, S. L., el al., "Radiographic Assessment of Posterolateral Spine Fusion With and Without Platelet Rich Plasma," 117, Abstracts of the 30th Annual Meeting of the International Society for the Study of the Lumbar Spine, Vancouver, Canada (May 2003).

Ezra, A., and Golomb, G., "Administration Routes and Delivery Systems of Bisphosphonates for the Treatment of Bone Resorption," *Adv. Drug Del. Rev.*, 42:175-195 (2000).

Frain, J., et al., "Use of cDNA Microarrays to Investigate Cytokine Expression in Intervertebral Disc Degeneration," 126, Abstracts of the 30th Annual Meeting of the International Society for the Study of the Lumbar Spine, Vancouver, Canada (May 2003).

Ganey, T. M. and Meisel, H. J., "A Potential Role for Cell-Based Therapeutics in the Treatment of Intervertebral Disc Herniation," *Eur. Spine J.*, 11 (Suppl. 2): S206-S214 (2002).

Goodman, S. et al., "Effects of Local Infusion of TGFβ on Bone Ingrowth in Rabbit Chambers," *J. Biomed. Mat. Res. (Appl Biomater)*, 53:475-479 (2000).

Goupille, P. et al., "Matrix Metalloproteinases: The Clue to Intervertebral Disc Degeneration?," *Spine*, 23(14): 1612-1626 (1998).

Kawakami, et al., "Role of IL-8, MCP-1 and PH in Neuropathic Pain Enhanced by Degenerative Nucleus Pulposus," 127, Abstracts of the 30th Annual Meeting of the International Society for the Study of the Lumbar Spine, Vancouver, Canada (May 2003).

Hunter, C. J., et al., "Functional Behavior of Notochordal Cell Clusters in the Canine Nucleus Pulposus: Cell Communication and Survival," 70, Abstracts of the 30th Annual Meeting of the International Society for the Study of the Lumbar Spine, Vancouver, Canada (May 2003).

Hydrogels, Encyclopedia of Polymer Science and Technology, (Wiley and Sons, 2003).

Imai, Y., et al., "Effect of Recombinant Human Osteogenic Protein-1 on Extracellular Matrix Metabolism by Human Annulus Fibrosus and Nucleus Pulposus Cells," 205, Abstracts of the 30th Annual Meeting of the International Society for the Study of the Lumbar Spine, Vancouver, Canada (May 2003).

Imai, Y., et al., "The Quantification of Cytokine-Induced Matrix Catabolism in Tissue Engeneered Intervertebral Discs," 67, Abstracts of the 30th Annual Meeting of the International Society for the Study of the Lumbar Spine, Vancouver, Canada (May 2003).

Inui, Y., et al., "Fas-Ligand Expression on Nucleus Pulposus Cells Begins in Developing Embryo," 42, Abstracts of the 30th Annual Meeting of the International Society for the Study of the Lumbar Spine, Vancouver, Canada (May 2003).

Karppinen, J., et al., "Tumor Necrosis Factor-α Monoclonal Antibody, Infliximab, Used to Manage Severe Sciatica," *Spine*, 28(8):750-754 (2003).

Kato, H., et al., "The Effect of IL-1 on the Rabbit Intervertebral Disc In Vivo," 199, Abstracts of the 30th Annual Meeting of the International Society for the Study of the Lumbar Spine, Vancouver, Canada (May 2003).

Kimble, R.B., et al., "Estrogen Deficiency Increases the Ability of Stromal Cells to Support Murine Osteoclastogenesis Via an InterLeukin-1 and Tumor Necrosis Factor-Mediated Stimulation of Macrophage Colony-Stimulating Factor Production," *J. Biol. Chem.* 271(46):28890-28897 (1996).

Kimble, R.B., et al., "The Functional Block of TNF but Not of IL-6 Prevents Bone Loss in Ovariectomized Mice," *J. Bone Min. Res.*, 12(6):935-941 (1997).

Koch, H., et al., "Spontaneous Secretion of Interleukin 1 Receptor Antagonist (IL-1Ra) by Cells Isolated from Herniated Lumbar Discal Tissue After Discectomy," *Cytokine*, 10(9): 703-705 (1998).

Korhonen, T., et al., "Efficacy of Infliximab for Disc Herniation-Induced Sciatica One-Year Follow-Up," 14, Abstracts of the 30th Annual Meeting of the International Society for the Study of the Lumbar Spine, Vancouver, Canada (May 2003).

Kozbor, D. and Roder, J.C., "The Production of Monoclonal Antibodies from Human Lymphocytes," *Immunol. Today*, 4(3):72-79 (1983).

Kwon, U-H., et al., "Dexamethsone Stimulates Cellular Proliferation While Downregulates Matrix Synthesis in Intervertebral Disc Cells," 29, Abstracts of the 30th Annual Meeting of the International Society for the Study of the Lumbar Spine, Vancouver, Canada (May 2003).

Lane, N.E., et al., "Basic Fibroblast Growth Factor Forms New Trabeculae that Physically Connect with Pre-Existing Trabeculae, and This New Bone is Maintained with an Anti-Resorptive Agent and Enhanced with an Anabolic Agent in an Osteopenic Rat Model," *Osteoporos. Int.*, 14:374-382 (2003).

La Van, et al., "Small-scale Systems for In Vivo Drug Delivery," *Nature Biotechnology* 21:1184-1191 (2003).

Lehman, et al., "Thalidomide Therapy for Recalcitrant Systemic Onset Juvenile Rheumatoid Arthritis," *J. Pediatrics*, 140: 125-7 (2002).

Le Maitre, C. L., et al., "Expression of the IL-1 Family in Human Intervertebral Disc," 217, Abstracts of the 30th Annual Meeting of the International Society for the Study of the Lumbar Spine, Vancouver, Canada (May 2003).

Le Maitre, C. L., et al., "Response of Human Intervertebral Disc Cells to IL-1," 216, Abstracts of the 30th Annual Meeting of the International Society for the Study of the Lumbar Spine, Vancouver, Canada (May 2003).

Le Visage, C., et al., "Interaction of Human Mescenchymal Stem Cells with Disc Cells: Changes in Biosynthesis of Extracellular Matrix," 25, Abstracts of the 30th Annual Meeting of the International Society for the Study of the Lumbar Spine, Vancouver, Canada (May 2003).

Lee, C. S., et al., "A Single Period of Hyperphysiologic Stretch Induces IL-6, TGF-beta and Cell Proliferation in Anulus Fibrosus Cells," 215, Abstracts of the 30th Annual Meeting of the International Society for the Study of the Lumbar Spine, Vancouver, Canada (May 2003).

Li, J., et al., "The Effects of Bone Morphogenetic Protein 2 (BMP-2) and Cartilage-Derived Morphogentic Protein 2 (CDMP-2) on Aggrecan Gene Expression in Chondrocytes," 30, Abstracts of the 30th Annual Meeting of the International Society for the Study of the Lumbar Spine, Vancouver, Canada (May 2003).

Lotz, J. C., et al., "Cytokines in Normal, Degenerated, and Nucleoplasty-Treated Porcine Discs," 157, Abstracts of the 30th Annual Meeting of the International Society for the Study of the Lumbar Spine, Vancouver, Canada (May 2003).

Meijer, H., et al., "The Production of Anti-Inflammatory Cytokines in Whole Blood by Physico-Chemical Induction," *Inflamm. Res.*, 52: 404-407 (2003).

Miyamoto, H., et al., "The Effect of Mechanical Stress on the Production of Inflammatory Agents by Disc Cells," 110, Abstracts of the 30th Annual Meeting of the International Society for the Study of the Lumbar Spine, Vancouver, Canada (May 2003).

Molloy, et al., "The Roles of Growth Factors in Tendon and Ligament Healing," *Sports. Med. 33*: 381-394 (2003).

Müller, R. "Determination of Affinity and Specificity of Anti-Hapten Antibodies by Competitive Radioimmunoassay," *Meth. Enzymol.*, 92:589-601 (1983).

Nakamura, K., et al., "Local Application of Basic Fibroblast Growth Factor into the Bone Increases Bone Mass at the Applied Site in Rabbits," *Arch. Orthop. Trauma Surg.*, 115(6):344-346 (1996).

Nakamura, K., et al., "Stimulation of Endosteal Bone Formation by Local Intraosseous Application of Basic Fibroblast Growth Factor in Rats," *Rev. Rhum.* [*Engl. Ed.*], 64(2):101-105 (1997).

Nikas, S.N., et al., "Treatment of Resistant Rhematoid Arthritis by Intra-Articular Infliximab Injections: A Pilot Study," *Ann Rheum Dis* 63: 102-103 (2004).

Ohtori, S., et al., "TNF-α and TNF-α Receptor 1 Upregulation in GLIA and Neurons After Nerve Injury. Studies in Murine DRG and Spinal Cord," 13, Abstracts of the 30th Annual Meeting of the International Society for the Study of the Lumbar Spine, Vancouver, Canada (May 2003).

Ohtori, S., et al., "TNF-α-Deficient Mice Have Fewer Macrophages in Injured Nerve and Reduced Glial Activation in DRG and Spinal Cord," 250, Abstracts of the 30th Annual Meeting of the International Society for the Study of the Lumbar Spine, Vancouver, Canada (May 2003).

Okuma, M., et al., "Rotary Cell Culture System Stimulates Annulus Fibrosus Cell Proliferation but Suppresses Proteoglycan Metabolism," 164, Abstracts of the 30th Annual Meeting of the International Society for the Study of the Lumbar Spine, Vancouver, Canada (May 2003).

Pacifici, R., "Editorial: Cytokines, Estrogen, and Postmenopausal Osteoporosis—The Second Decade," *Endocrinology*, 139(6):2659-2661 (1998).

Pederson, A.W., et al., "Thermal Assembly of a Biomimetic Mineral/Collagen Composite," *Biomaterials*, 24:4881-4890 (2003).

Richardson, S., et al., "Human Bone Marrow Mesenchymal Stromal Cells as a Source of Chondrocytes for Treatment of Intervertebral Disc Degeneration," 27, Abstracts of the 30th Annual Meeting of the International Society for the Study of the Lumbar Spine, Vancouver, Canada (May 2003).

Risbud, M. V., et al., "Mesenchymal Stem Cells Respond to Their Microenvironment In Vitro to Assume-Nucleus Pulposus-Like Phenotype," 26, Abstracts of the 30th Annual Meeting of the International Society for the Study of the Lumbar Spine, Vancouver, Canada (May 2003).

Rodan, G.A., et al., "Therapeutic Approaches to Bone Diseases," *Science*, 289:1508-1514 (2000).

Sakai, D., et al., "Autologous Transplantation of Mesenchymal Stem Cells for Disc Repair," 24, Abstracts of the 30th Annual Meeting of the International Society for the Study of the Lumbar Spine, Vancouver, Canada (May 2003).

Sakai, D., et al., "Transplantation of Mesenchymal Stem Cells Embedded in Atelocollagen® Gel to the Intervertebral Disc: A Potential Therapeutic Model for Disc Degeneration," *Biomaterials*, 24: 3531-3541 (2003).

Schatteman, L., et al., "Treatment of Refractory Inflammatory Monoarthritis in Ankylosing Spondylitis by Intraarticular Injection of Infliximab," *The Journal of Rheumatology*, 33:1 82-85 (2006).

Sobajima, S., et al., "Stem Cell Therapy for Degenerative Disc Disease: An In-Vitro Feasibility Study," 43, Abstracts of the 30th Annual Meeting of the International Society for the Study of the Lumbar Spine, Vancouver, Canada (May 2003).

Stern, S., et al., "Human Intervertebral Disc Cell Culture for Disc Disorders," *Clin. Orthop.*, 419:238-244 (2004).

Takada, T., et al., "IL-6 Production was Upregulated by Interaction Between Disc Tissue and Macrophages," 41, Abstracts of the 30th Annual Meeting of the International Society for the Study of the Lumbar Spine, Vancouver, Canada (May 2003).

Takegami, K., et al., "Osteogenic Protein-1 Enhances Matrix Replenishment by Intervertebral Disc Cells Previously Exposed to Interleukin-1," *Spine*, 27(12):1318-1325 (2002).

Tobinick, E.L. "Targeted Etanercept for Discogenic Neck Pain: Uncontrolled, Open-Label Results in Two Adults," *Clin. Thera.*, 25(4):1211-1218 (2003).

Tsuji, T., et al., "Age-Related Changes in M-RNA Expression of Various Regulatory Factors in Rabbit Intervertebral Disc," 81, Abstracts of the 30th Annual Meeting of the International Society for the Study of the Lumbar Spine, Vancouver, Canada (May 2003).

Vahle, J.L., et al., "Skeletal Changes in Rats Given Daily Subcutaneous Injections of Recombinant Human Parathyroid Hormone (1-34) for 2 Years and Relevance to Human Safety," *Toxicol. Pathol.*, 30(3):312-321 (2002).

Weiler, C., et al., "Expression of TNF-α in Autopsy and Biopsy Specimens of Intervertebral Discs of Various Age and Degeneration," 233, Abstracts of the 30th Annual Meeting of the International Society for the Study of the Lumbar Spine, Vancouver, Canada (May 2003).

Xie, X., et al., "Treatment of Spondylodiscitis Intravenous Versus Percutaneous Intradiscal Applications of Antibiotics: An Experimental Study in Rabbits," 120, Abstracts of the 30th Annual Meeting of the International Society for the Study of the Lumbar Spine, Vancouver, Canada (May 2003).

Yabuki, S., et al., "Prevention of Compartment Syndrome in Dorsal Root Ganglia Caused by Exposure to Nucleus Pulposus," *Spine*, 26(8):870-875 (2001).

Yaffe, A., et al., "Combined Local Application of Tetracycline and Bisphosphonate Reduces Alveolar Bone Resporption in Rats," *J. Periodontol*, 74:1038-1042 (2003).

Yoon, S. T., et al., "LMP-1 Upregulates Proteoglycan Synthesis in Intervertebral Disc Cells Through a BMP Mediated Process," 31, Abstracts of the 30th Annual Meeting of the International Society for the Study of the Lumbar Spine, Vancouver, Canada (May 2003).

Ohno, K. and Oshita, S., "Transdiscal Lumbar Sympathetic Block: A New Technique for a Chemical Sympathectomy," *Anesth. Analg.*, 85:1312-1316 (1997).

Tanny, G.B. et al., "Improved Filtration Technique for Concentrating and Harvesting Bacteria," *Appl. Environ. Microbiol.*, 40(2):269-273 (1980).

Raucci, A. et al., "Activation of the ERK1/2 and p38 Mitogen-Activated Protein Kinase Pathways Mediates Fibroblast Growth Factor-Induced Growth Arrest of Chondrocytes," *J. Biol. Chem.*, 279(3):1747-1756 (2004).

Marriott, J.B. et al., "CC-3052: A Water-Soluble Analog of Thalidomide and Potent Inhibitor of Activation-Induced TNF-α Production," *J. Immunol.*, 161:4236-4243 (1998).

Hawks, D., "Alternative Medicine: Musculoskeletal System," *Clin. Tech. Small Anim. Pract.*, 17(1):41-49 (2002).

Khot, A. et al., "The Use of Intradiscal Steroid Therapy for Lumbar Spinal Discogenic Pain—A Randomized Controlled Trial," *Spine*, 29(8):833-837 (2004).

Földes, I. et al., "Trace Elements in Tissues of Normal and Vitamin $D_2$-Treated Rats," *ACTA Biol. Acad. Sci. Hung.*, 26(3-4):141-150 (1975).

CN 1 647 808 A (Zhou C) Aug. 3, 2005 (abstract) World Patents Index [online]. London, GB: Derwent Publications, Ltd., Week 200621, Accession No. 2006-194507.

CN 1 569 039 A (Niu X) Jan. 26, 2005 (abstract) World Patents Index [online]. London, GB: Derwent Publications, Ltd., Week 200577, Accession No. 2005-749289.

Tracey, K.J. and Cerami, A., "Tumor Necrosis Factor in Metabolism of Disease: Hormonal Actions Versus Local Tissue Effects," *Nouv. Rev. Fr. Hematol.*, 34 Suppl:S37-42 (1992) (abstract).

Crevensten, G. et al., "Intervertebral Disc Cell Therapy for Regeneration: Mesenchymal Stem Cell Implantation in Rat Intervertebral Discs," *Ann. Biomed. Eng.*, 32(3):430-434 (2004).

Ceponis, A. et al. "Effects of Low-Dose, Noncytotoxic, Intraarticular Liposomal Clodronate on Development of Erosions and Proteoglycan Loss in Established Antigen-Induced Arthritis in Rabbits,"*Arthritis and Rheum.*, 44(8): 1908-1916 (2001).

Chan, J.M.K. et al., "Intraarticular Gene Transfer of TNFR:Fc Suppresses Experimental Arthritis with Reduced Systemic Distribution of the Gene Product," *Mol. Ther.*, 6(6): 727-736 (2002).

Kim, S.H. et al. "Ex Vivo Gene Delivery of IL-1Ra and Soluble TNF Receptor Confers a Distal Synergistic Therapeutic Effect in Antigen-Induced Arthritis," *Mol. Ther.*, 6(5): 591-600 (2002).

Lubberts, E. et al., "Intra-Articular IL-10 Gene Transfer Regulates the Expression of Collagen-Induced Arthritis (CIA) in the Knee and Ipsilateral Paw," *Clin. Exp. Immunol.*, 120:375-383 (2000).

Niccoli, L. et al., "Intraarticular Injection of Infliximab in Relapsing Knee Effusion in Psoriatic Arthritis: A Pilot Study," *Ann. Rheum. Dis.*, 62(1); 239-240 (2003) and EULAR—Annual European Congress of Rheumatology, Lisbon, Portugal (2003) (abstract).

Nikas, S.N., et al., "Treatment of Resistant Rheumatoid Arthritis by Intra-Articular Injections with Infliximab: A Pilot Study," *Ann. Rheum. Dis.* 62(1): 408 (2003) and EULAR—Annual European Congress of Rheumatology, Lisbon, Portugal (2003) (abstract).

Steer, J.H. et al., "Altered Leucocyte Trafficking and Suppressed Tumour Necrosis Factor α Release from Peripheral Blood Monocytes After Intra-Articular Glucocorticoid Treatment," *Ann. Rheum. Dis.*, 57(12): 732-737 (1998).

Williams, A.S. et al., "Amelioration of Rat Antigen-Induced Arthritis by Liposomally Conjugated Methotrexate is Accompanied by Down-Regulation of Cytokine mRNA Expression," *Rheumatology*, 40:375-383 (2001).

Haro, H. et al., "Matrix Metalloproteinase-7-Dependent Release of Tumor Necrosis Factor-α in a Model of Herniated Disc Resorption," *J. Clin. Invest.*, 105(2):143-150 (2000).

Abbas-Ghaleb, K., et al., "Preconcentration of Selenium Compounds on a Porous Graphitic Carbon Column in view of HPLC-ICP-AES Speciation Analysis," *Anal. Bioanal. Chem.*, 377: 1026-1031 (2003).

Awasthi, Y., et al., "Purification and Properties of Human Erythrocyte Glutathione Peroxidase," *J. Biol. Chem.*, 250(13): 5144-5149 (1975).

Biemond, P., et al., "Protective Factors Against Oxygen Free Radicals and Hydrogen Peroxide in Rheumatoid Arthritis Synovial Fluid," *Arthritis Rheum.*, 27(7): 760-765 (1984).

Castro, R., et al., "Failure of Bone Marrow Cells to Transdifferentiate Into Neural Cells in Vivo," *Science*, 297: 1299 (2002).

Desai, S., et al., "Coated Microwell Plate-based Affinity Purification of Antigens," *Anal. Biochem.*, 328: 162-165 (2004).

El-Khoury, G., et al., "Percutaneous Procedures for the Diagnosis and Treatment of Lower Back Pain: Diskography, Facet-joint Injection, and Epidural Injection," *AJR*, 157(4): 685-691 (1991).

Gori, A. et al., "Tumor necrosis Factor-α Increased Production during Thalidomide Treatment in Patients with Tuberculosis and Human Immunodeficiency Virus Coinfection," *Journal of Infectious Diseases*, 182:639-640 (2000).

Guillen, C., et al.,"The Effects of Local Administration of Lactoferrin on Inflammation in Murine Autoimmune and Infectious Arthritis," *Arthritis Rheum.*, 43(9): 2073-2080 (2000).

Hayashida, K., et al., "Lactoferrin Enhances Peripheral Opioid-mediated Antinociception via Nitric Oxide in Rats," *Eur. J. Pharmacol.*, 484: 175-181 (2004).

Hayashida, K., et al.,"Oral Administration of Lactoferrin Inhibits Inflammation and Nociception in Rat Adjuvant-induced Arthritis," *J. Vet. Med. Sci.*, 66(2): 149-154(2004).

Kamanh, A., et al., "Plasma Lipid Peroxidation and Antioxidant Levels in Patients with Rheumatoid Arthritis," *Cell Biochem. Funct.*, 22: 53-57 (2004).

Kilic, B., et al., "Effects of Intra-articular Vitamin E and Corticosteroid Injection in Experimental Hemarthrosis in Rabbits," *Pediatr. Hematol. Oncol.*, 15(4): 339-346(1998).

Kurz, B., et al., "Dietary Vitamins and Selenium Diminish the Development of Mechanically Induced Osteoarthritis and Increase the Expression of Antioxidative Enzymes in the Knee Joint of STR/IN Mice," *Osteoarthritis Cartilage*, 10: 119-126 (2002).

Maddipati, K., et al., "Characterization of the Major Hydroperoxide-reducing Activity of Human Plasma," *J. Biol. Chem.*, 262(36): 17398-17403 (1987).

Martinez, J., et al., "Blood Platelet Glutathione Peroxidase: Some Properties and Partial Purification," *Thromb. Res.*, 19: 73-83 (1980).

McMillan, D., et al., "Intra-operative Autologous Blood Management," *Transfusion and Apheresis Science*, 27(1): 73-81 (2002).

Salin, M., et al., "Free Radicals and Inflammation: Protection of Phagocytosing Leukocytes by Superoxide Dismutase," *J. Clin. Invest.*, 56: 1319-1323 (1975).

Schalkwijk, J., et al., "Cationization of Catalase, Peroxidase, and Superoxide Dismutase," *J. Clin. Invest.*, 76: 198-205 (1985).

Stepanik, T., et al., "Coisolation of Glutathione Peroxidase, Catalase and Superoxide Dismutase from Human Erythrocytes," *J. Biochem. Biophys. Methods*, 20: 157-169 (1990).

Tiku, M., et al., "Aggrecan Degradation in Chondrocytes is Mediated by Reactive Oxygen Species and Protected by Antioxidants," *Free Radic. Res.*, 30: 395-405 (1999).

Tiku, M., et al., "Evidence Linking Chondrocyte Lipid Peroxidation to Cartilage Matrix Protein Degradation," *J. Biol. Chem.*, 275(26): 20069-20076 (2000).

Tobinick, E., "Targeted Etanercept for Treatment-refractory Pain Due to Bone Metastasis: Two Case Reports," *Clinical Therapeutics.*, 25(8): 2279-2288 (2003).

Trif, M., et al., "Liposomes as Possible Carriers for Lactoferrin in the Local Treatment of Inflammatory Diseases," *Exp. Biol. Med.*, 226(6): 559-564 (2001).

Yang, J., et al., "Purification and Quantitation of a Rat Plasma Selenoprotein Distinct from Glutathione Peroxidase Using Monoclonal Antibodies," *J. Biol. Chem.*, 262(27): 13372-13375 (1987).

Notification of Transmittal of the International Search Report and the Written Opinion of the International Searching Authority, or the Declaration, International Application No. PCT/US2004/024725, date of mailing Jun. 7, 2005.

Notification Concerning Transmittal of International Preliminary Report on Patentability, International Application No. PCT/US2004/024725, date of mailing Feb. 9, 2006.

Ando, N., et al., "An Immunohistochemical Study of the Degenerative Lumbar Disc," *Orthopedics & Traumatology* 44(1): 176-178 (1995) (Published in Japanese with English Abstract).

Schaible, H-G, et al., "The Role of Proinflammatory Cytokines in the Generation and Maintenance of Joint Pain," *Ann. N.Y. Acad. Sci.* 1193:60-69 (2010).

Yorimitsu, E., "A Comparative Study on the Pathological Changes of Intervertebral Discs after Intradiscal Injection of Various Kinds of Steroid Materials: An Experimental Study," *Journal Keio Medical Society* 74(5): 303-315 (1997) (Published in Japanese with English Abstract).

Office Action, U.S. Appl. No. 12/005,069, dated Dec. 8, 2010.

Office Action (RR), U.S. Appl. No. 12/005,069, dated Aug. 23, 2010.

International Preliminary Report on Patentability, PCT/US2004/024725, mailed Feb. 9, 2006.

International Search Report and Written Opinion, PCT/US2004/024725, mailed Jun. 7, 2005.

Invitation to Pay Additional Fee with the Partial International Search, PCT/US2004/024725, mailed Mar. 7, 2005.

Communication pursuant to Article 94(3) EPC, EP 04 779 700.6, dated Aug. 18, 2009.

Communication with European Search Report, EP 04 779 700.6, dated Sep. 26, 2007.

Communication under Rule 112 EPC, EP 04 779 700.6, dated May 2, 2007.

European Patent Office, Summons to attend oral proceedings pursuant to Rule 115(1) EPC, European Patent Application No. 04776014.5, dated May 20, 2010.

* cited by examiner

TRANS-CAPSULAR ADMINISTRATION OF HIGH SPECIFICITY CYTOKINE INHIBITORS INTO ORTHOPEDIC JOINTS

BACKGROUND OF THE INVENTION

The natural articulating joint (diarthrodal joint) comprises adjacent bones having opposing hyaline cartilage surfaces held together by a fibrous collagenous capsule defining a joint space. The inner wall of this capsule is lined with synovial cells. Contained within the capsular joint space is an acellular synovial fluid. The function of the synovial fluid is to provide lubrication for the articulating surfaces.

In a healthy joint, cells within the articular cartilage produce an extracellular matrix (ECM) containing a high percentage of proteoglycans. These proteoglycans contain sulfated functional groups that retain water, thereby providing the cartilage with its lubricating qualities. These cells may also secrete small amounts of cytokines as well as matrix metalloproteinases ("MMPs"). These cytokines and MMPs help regulate the metabolism of the hyaline cartilage cells.

There appear to be many causes of degenerative joint disease (DJD). For example, gradual degeneration of the joint may be caused by wear, by trauma, by misalignment, by genetics, or by mechanical instabilities in other portions of the body. In many instances, gradual wear of the hyaline cartilage cause the cells therein (or invading macrophages) to emit larger than normal amounts of the above-mentioned cytokines. In other instances of DJD, genetic factors, such as programmed cell death, or apoptosis can also cause the cells within the hyaline cartilage to emit abnormally large amounts of these cytokines into the extracellular matrix of the hyaline cartilage and synovial fluid.

Although the progression of DJD (also called "osteoarthritis", or "OA") is largely dependent upon etiology, it is often the case that the high levels of the cytokines present in the hyaline cartilage begin to mediate the degradation of the extracellular matrix of the cartilage. Concurrently, enzymes in the synovial fluid both upregulate MMPs and downregulate MMP inhibitors. The MMPs (under mediation by the cytokines) begin cleaving the water-retaining portions of the proteoglycans, thereby reducing its water-retaining and lubricious qualities. This degradation leads to a less lubricious hyaline cartilage, thereby increasing the wear upon the hyaline cartilage. This degenerative cascade also often leads to inflammation of the synovial lining, which often produces a thickening and fibrillation of the synovium, and the creation of finger-like villae with the synovium. When the natural regeneration of these cartilage layers is slower than this degenerative process, these changes cause even more mechanical instability, thereby causing the hyaline cartilage cells, the synovium cells and the invading macrophages to emit even more cytokines, thereby typically upregulating MMPs.

In addition to the foregoing, posterior elements of the spine called the "facet joints" help to support axial, torsional and shear loads that act on the spinal column. Furthermore, the facet joints are diarthroidal joints that provide both sliding articulation and load transmission features. The facet's articular surfaces contact in extension, limiting rotation and increasing compressive load. The articular surfaces also contact on one side of the spine in lateral bending and axial rotation, also limiting rotation and transferring load. Early facet osteoarthrosis is relatively mild and is confined to the articular cartilage, capsule, and synovium, but eventually involves the subchondral bone and the margins equally on both sides of a motion segment. With advancing degeneration, the joint capsule undergoes significant changes including increasing fibrosis and vascularization, which has been reported to become hyperemic with infiltration of inflammatory cells, enlargement, and fibrosis.

The posterior zygo-apophyseal joints (facet joints) may be a significant source of spinal disorders and, in many cases, debilitating pain. The articular cartilaginous surfaces can degenerate due to mechanical or biological factors and cause pain as with other joint osteoarthritis. Synovial cysts of the facet joints occur most commonly in association with degenerative disease of the spine in older individuals. The association of these cysts with trauma, rheumatoid arthritis, spondylolysis and kissing spinous processes also has been reported. These cysts can cause symptoms and signs from direct compression of the dura. For example, a patient may suffer from arthritic facet joints, severe facet joint tropism or otherwise deformed facet joints, facet joint injuries, etc. There is currently a lack of suitable intervention procedures for facet joint disorders. Facet blocks with anesthetic and cortisone, facet denervation procedures, radiofrequency ablation of the nerve supply to the joint, or even spinal fusions have been recommended. In the early stages of degeneration, pain may be controlled by blocking the medial branch of the lumbar zygapophyseal (facet) joints (kryorhizotomy). However, this treatment mode of treatment is considered for temporary relief of pain. Facetectomy, or the removal of the facet joints, may provide some relief, but is also believed to significantly decrease the stiffness of the spinal column (i.e., hypermobility) in all planes of motion: flexion and extension, lateral bending, and rotation. Furthermore, problems with the facet joints can also complicate treatments associated with other portions of the spine. By way of example, contraindications for artificial discs include arthritic, deformed, unstable, or painful facet joints. Accordingly, there is a need for a facet joint treatment that addresses these concerns.

Accordingly, there is a need for a minimally invasive treatment of facet joints.

Braun, *Expert Opin. Biol. Ther.* 3(1):141-168 (2003) ("Braun I") reviews the efficacy of infliximab, a high specificity antagonist of TNF-α, in treating chronic inflammatory diseases. Braun reports that infliximab is delivered through essentially systemic administration routes. Braun does not report any local administration routes.

Braun, *Ann. Rheum. Dis.*, 61 (Supp. III):,iii51-iii60 (2002), reviews the international experience of the use of anti-TNF α therapy for ankylosing spondylitis. Braun II reports that anti-TNF-α drugs are delivered through essentially systemic administration routes. Braun II does not report any local administration routes.

Olmarker, *Spine,* 26(8):863-9 (2001) ("Olmarker I") and Aoki, *Spine,* 27(15):1614-17 (2002) teach that TNF-α appears to play a role in the producing the pain associated with the nucleus pulposus contacting nerve roots of the spinal cord.

U.S. Published Patent Application No. US 2003/0039651 ("Olmarker II") teaches a therapeutic treatment of nerve disorders comprising administration of a therapeutically effective dosage of at least two substances selected from the group consisting of TNF inhibitors (both specific and non-specific), IL-1 inhibitors, IL-6 inhibitors, IL-8 inhibitors, FAS inhibitors, FAS ligand inhibitors, and IFN-gamma inhibitors. In the examples of Olmarker II, it is taught that these substances are to be administered through systemic pathways. In particular, Olmarker II teaches that "the major contribution of TNF-alpha may be derived from recruited, aggregated and maybe even extravasated leukocytes, and that successful pharmacologic block may be achieved only by systemic treatment".

U.S. Pat. No. 6,419,944 ("Tobinick I") discloses treating herniated discs with cytokine antagonists, including infliximab. However, Tobinick teaches that local adminstration involves an extradiscal injection between the disc and spinal cord. Accordingly, Tobinick does not teach a procedure involving directly administering a specific cytokine antagonist (such as infliximab) into a capsuled space.

U.S. Published Patent Application No. 2003/0049256 (Tobinick II) discloses that injection of such therapeutic molecules to the anatomic area adjacent to the spine is accomplished by interspinous injection, and preferably is accomplished by injection through the skin in the anatomic area between two adjacent spinous processes of the vertebral column.

Tobinick II discloses several spine and orthopaedic applications: Spinal Cord Injury (#12); neuropathic pain (#14); lumbar and Cervical Radiculopathy (#15); low back pain (#17), and Vertebral Disc Disease (#19). Tobinick teaches a parenteral/perispinal route of administration for spinal cord injuries; a perispinal route of administration for neuropathic pain; a perispinal route of administration for lumbar and Cervical Radiculopathy; a parenteral/perispinal route of administration for low back pain; and a perispinal route of administration for Vertebral Disc Disease. In each of applications Nos. 14, 15, 17 and 19, Tobinick appears to teach that the disc must be herniated, torn or leaking and so an extruded nucleus pulposus is the target tissue.

Tobinick II further teaches that TNF antagonists may be administered by interspinous injection in the human and that the dosage level is in the range of 1 mg to 300 mg per dose, with dosage intervals as short as two days. Tobinick II further discloses that Interleukin-1 antagonists are administered in a therapeutically effective dose, which will generally be 10 mg to 200 mg per dose, and their dosage interval will be as frequent as once daily.

Tobinick, *Swiss Med. Weekly,* 133:170-77 (2003), ("Tobinick III") teaches both perispinal and epidural administration of TNF inhibitors for spine related therapies.

Alini, *Eur. Spine J.,* 11(Supp.2):S215-220 (2002), teaches therapies for early stage disc degeneration disease, DDD, including injection of inhibitors of proteolytic enzymes or biological factors that stimulate cell metabolic activity (i.e., growth factors) in order to slow down the degenerative process. Alini I does not teach any similar injections into joints having synovial fluid.

U.S. Published Patent Application US2002/0026244 ("Trieu") discloses an intervertebral disc nucleus comprising a hydrogel that may deliver desired pharmacological agents. Trieu teaches that these pharmacological agents may include growth factors such as TGF-B and anti-inflammatory drugs, including steroids. Trieu further teaches that these pharmacological agents may be dispersed within the hydrogel having an appropriate level of porosity to release the pharmacological agent at a desired rate. Trieu teaches that these agents may be released upon cyclic loading or upon resorption. Trieu does not teach any similar injections into joints having synovial fluid.

Maeda et al. *Spine,* 25(20):166-169 (2000), reports on the in vitro response to interleukin-1 receptor antagonist protein (IRAP) of rabbit annulus fibrosus exposed to IL-1. Maeda suggests that IRAP could be useful in inhibiting the degradation of the disc. Maeda does not teach any similar utility for joints having synovial fluid.

Igarashi et al., ISSLS Abstract #262 (May 13-17, 2003), sought to quantify the levels of various cytokines present within the facet joints of patients suffering from low back pain and sciatica. Igarashi appears to report that the levels of TNF-α were below the detection limits of the assay, but that the higher levels of IL-1β (for the patients with lumbar canal stenosis), and IL-6 were each statistically significant.

EP 1153607 A2 ("Dunn") discloses injecting anti-cytokines (and in particular, an anti-TNF antibody called "Enbrel™", which binds only soluble TNF), anti-kinases, anti-proteases, and anti-growth factors into orthopaedic joints, including those of the vertebrae. Dunn also discloses that these agents may be administered with a lubricant, such as hyaluronic acid.

U.S. Pat. No. 5,095,037 ("Iwamitsu") discloses local administration of a composition comprising (a) an effective amount of hyaluronic acid or its salt, and (b) an effective amount of an anti-inflammatory agent. Iwamitsu particularly discloses Diclofenac, a COX-2 enzyme inhibitor, as one suitable anti-inflammatory agent.

WO 03/000190 A2 ("Thompson") discloses a composition comprising glycosaminoglycans encapsulated in a liposomal delivery system for intra-articular administration for the treatment of osteoarthritis. Thompson further teaches that the composition may further include additional benefit agents such as p38 kinase inhibitors, TNF inhibitors, and inhibitors of enzymes that are involved in the destruction of articulating joints and synovial fluid components (such as hyaluronidase inhibitors, MMP inhibitors, aggrecanse inhibitors, or apoptosis inhibitors such as EPO), and cartilage enhancing factors such as TGF-β and BMP. Thompson does not specifically teach p38 kinase inhibitors having high specificity towards p38 kinase.

Certain molecules, such as tetravalent guanylhydrazone, non-specifically inhibit p38 kinase.

Wittenberg et al., *Arthritis Rheum.,* 36(10):1444-50 (October 1993) investigated the major source of eicosanoid release in arthritic joint tissues. Release of prostaglandin E2 (PGE2), 6-keto-PGF1 alpha, leukotriene B4 (LTB4), and LTC4 were measured. Wittenberg reported in vitro experiments showing that the PG release was significantly inhibited by the addition of indomethacin or diclofenac (a COX-2 enzyme inhibitor) at either $10^{-5}$ moles/liter or $10^{-7}$ moles/liter. Wittenberg concluded that synovial tissue appears to be the major source of eicosanoids in synovial fluid, and that indomethacin and diclofenac inhibit the release of PG, but not LT, from various joint tissues.

SUMMARY OF THE INVENTION

The present inventors have developed a number of localized procedures for efficaciously treating degenerative joint disease by drug therapy.

The present inventors believe that pro-inflammatory molecules within a joint capsule may contribute to degeneration of and/or pain within the joint in at least one of the following ways:
a) chemical sensitization of nerve fibrils contained within the collagenous ligaments of the joint capsule;
b) chemical sensitization of nerve fibrils contained within the synovium;
c) mediation of and/or direct degeneration of the hyaline articular surfaces; and
d) chemical sensitization of nerve fibrils adjacent or in close proximity to a joint capsule.

In accordance with the present invention, the present inventors have developed a method of treating inflamed joints in which an effective amount of a high specificity antagonist of a pro-inflammatory molecule ("HSA") is administered transcapsularly (i.e., directly into an inflamed capsule). The high specificity antagonist (HSA) is selected from the group consisting of:
a) an inhibitor of a pro-inflammatory interleukin;
b) an inhibitor of TNF-α synthesis;
c) an inhibitor of membrane-bound TNF-α;
d) an inhibitor of a natural receptor of TNF-α;
e) an inhibitor of NO synthase;
f) an inhibitor of $PLA_2$ enzyme;
g) an anti-proliferative agent;
h) an anti-oxidant;
i) an apoptosis inhibitor selected from the group consisting of EPO mimetic peptides, EPO mimetibodies, IGF-I, IGF-II, and caspase inhibitors;
j) an inhibitor of MMPs; and
k) an inhibitor of p38 kinase.

There are believed to be several advantages to directly administering these therapeutic inhibitors trans-capsularly over the systemic treatments, such as those disclosed by Braun.

First, since cytokines such as interleukins and TNF-α play roles in mediating inflammatory reactions within the synovium or degradation of hyaline articular cartilage, injecting an antagonist or inhibitor of these proteins directly into a capsule prevents the target cytokine from inducing any inflammation. In effect, the intra-capsular adminstration of the cytokine antagonist arrests the inflammation process begun within the joint and the degeneration of the hyaline cartilage.

Second, nerve ending nociceptors are present both within the subchondral endplates of the joint and in the wall of the surrounding peripheral capsule. Additionally, dorsal root ganglion (DRG) neurons having dichotomizing axons are considered to be related to referred pain. Clinically, pain from the lumbar facet joint is sometimes referred to the lower extremities innervated by the sciatic nerve. This is primarily due to DRG neurons innervating the lumbar facet joints. Cytokines such as TNF-α, as well as prostaglandins and nitric oxide ("NO") irritate or mediate the irritation of such nerves. It is believed that locally administering a highly specific antagonist of these molecules into the capsule also prevents the target pro-inflammatory molecule from causing intracapsular nerve irritation. Thus, the pain attributed to irritation of these nerves can be efficiently eliminated or reduced.

Third, it is further believed that transcapsular administration of an effective amount of a high specificity antagonist of the $PLA_2$ enzyme would also help provide therapy to the patient having DJD. It is believed that the $PLA_2$ enzyme is a regulator of the production of prostaglandin, which itself has been implicated in pain generation. At least one high specificity antagonist of $PLA_2$ is disclosed in Kawakami, *Clin. Orthop.*, 351: 241-51(1998).

Fourth, it is further believed that transcapsular administration of an effective amount of a high specificity antagonist of the NO synthase enzyme would also help provide therapy to the patient having DJD. It is believed that the NO synthase enzyme regulates the production of NO, which is known to have pro-inflammatory effects and has been implicated in pain generation. Some high specificity antagonists of NO synthase are N-iminoethyl-L-lysine (L-NIL), and $N^G$-monomethyl-L-arginine.

Fifth, it is further believed that transcapsular administration of an effective amount of a high specificity anti-oxidant would also help provide therapy to the patient having DJD. It is believed that oxidants degrade the hyaline cartilage extracellular matrix. Typical anti-oxidants include free radical scavengers and superoxide dismutase enzymes.

Sixth, since the surrounding capsule portion of the joint comprises a relatively dense collagenous structure, this outer component of the joint may provide a suitable depot for the high specificity antagonist (HSA), thereby increasing its half-life in the capsule.

Seventh, since the high specificity antagonist inhibits only the specific molecule of interest, not only will unwanted side effects be reduced, but also the HSA may be combined with other therapeutic agents (such as TGF-β, or mesenchymal stem cells) that can also be injected into the capsule without the HSA reducing the effectiveness of those other agents.

Eighth, it is further believed that transcapsular administration of an effective amount of a high specificity anti-proliferative agent would also help provide therapy to the patient having DJD. It is believed that antiproliferative agents may have an effect on inflammation by effecting inflamed synovial tissues which would limit the production of inflammatory cytokines. In some embodiments, the high specificity anti-proliferative is selected from the group consisting of a) rapamycin; b) an inhibitor of cyclin dependent kinase 9 (cdk); and c) statins (such as MEVASTATIN™ and LOVASTATIN™). In one embodiment, when rapamycin is selected, it is believed that a dosage producing a local tissue concentration of between about 0.5 ug/kg and 50 ug/kg is preferred.

Rapamycin is a potent inhibitor of downstream signaling of TOR (target of Rapamycin) proteins. As such, it is responsible for coordinating the balance between protein synthesis and protein degradation. Osteoarthritis is known to be propagated by a loss of balance between extracellular matrix synthesis and degradation. Since TOR proteins regulate multiple metabolic pathways, it is believed that rapamycin may stabilize the balance of the cycle. Rapamycin may also directly effect the proliferation and subsequent immune reaction of synoviocytes. In addition, it is known that osteoarthritic chondrocytes demonstrate a low level of proliferative activity by contrast to normal articular chondrocytes which show no activity. This is thought to lead to chondrocyte clustering within the cartilage. Rapamycin could function to eliminate the atypical chondrocyte proliferation. Preferably, it is provided in a 0.1 to 10 μM dose.

A cdk inhibitor may directly effect the proliferation and subsequent immune reaction of synoviocytes. Cdk inhibitors may also have a direct effect on chondrocyte clustering which is known to be a characteristic osteoarthritic event. Exemplary cdk inhibitors include flavopiridol, roscovitine, and compounds disclosed in PCT Patent Publication No. WO 02/057240 (Lin) and U.S. provisional patent application 60/257,703, the specifications of which are incorporated by reference herein in their entirety. Preferably, it is provided in a 1 to 10 uM dose.

In addition, the present invention is directed to providing a highly specific anti-apoptosis molecule to the diseased joint. It is believed these molecules will serve to protect against chondrocyte apoptosis. Preferred compounds include erythropoetin mimetic peptides, EPO mimetibodies, IGF-I, IGF-II, and caspase inhibitors.

Lastly, the present invention is directed to providing a highly specific anti-matrix metalloproteinase (HAAMMP) to the diseased joint. Preferably, the HAAMMP is administered in an amount effective to inhibit the specific action of MMPs released by cells during the degenerative process.

In some embodiments, the HAAMMP is a natural inhibitor of MMPs (TIMP). Preferably, the TIMP is selected from the group consisting of TIMP-1 and TIMP-2. In some embodiments, the TIMP is autologous and is concentrated by filtration, centrifugation or by immuno-attachment processes. In other embodiments, the TIMP is manufactured recombinantly, and is preferably present in a concentration of at least 1000 times that found in the patient.

In some embodiments, the HAAMP comprises a chelating group that binds tightly to the zinc component present in the active site of the MMP. Such HAAMMPs may be selected from the materials disclosed in Gordon, *Clin. Exp. Rheumatol.*, (1993), 11(Supp 8): S91-4; and Johnson, *J., Enzyme Inhib.*, 2:1-22 (1987).

In some embodiments, the therapeutic substance is a specific antagonist of a collagenase MMP. In some embodiments, the therapeutic substance is a specific antagonist of a stromelysin MMP. In some embodiments, the therapeutic substance is a specific antagonist of a gelatinase MMP. In some embodiments, the therapeutic substance is a specific antagonist of a membrane MMP.

Preferably, the targeted MMP is selected from the group consisting MMP-2, MMP-3, MMP-13 and MMP-8. MMP3, MMP-8, and MMP-13 are all known to be present in higher levels in osteoarthritic cells. Targeting MMP-2 and/or MMP-3 is desirable because these MMPs are believed to degrade proteoglycans. Targeting MMP-8 is desirable because this MMP is believed to degrade aggrecans.

Accordingly, in a first aspect of the present invention, there is provided a method of treating an inflamed orthopedic joint comprising a) opposing hyaline cartilage articular surfaces, b) a peripheral collagenous capsule defining a central joint space and c) synovial fluid contained within the joint space, comprising: trans-capsularly administering into the joint space a formulation comprising an effective amount of a high specificity antagonist (HSA) selected from the group consisting of:
    i) an inhibitor of a pro-inflammatory interleukin;
    ii) an inhibitor of TNF-α synthesis;
    iii) an inhibitor of membrane-bound TNF-α;
    iv) an inhibitor of a natural receptor of TNF-α;
    v) an inhibitor of NO synthase;
    vi) an inhibitor of $PLA_2$ enzyme;
    vii) an anti-proliferative agent;
    viii) an anti-oxidant;
    ix) an apoptosis inhibitor selected from the group consisting of EPO mimetic peptides, EPO mimetibodies, IGF-I, IGF-II, and caspase inhibitors;
    x) an anti-matrix metalloproteinase (MMP); and
    xi) an inhibitor of p38 kinase.

DETAILED DESCRIPTION OF THE INVENTION

For the purposes of the present invention, the terms "inhibitor" and "antagonist" are used interchangeably. A protein may be inhibited at the synthesis level, at the translation level, by shedding, by antibodies, or, in some cases, by soluble receptors. The term "patient" refers to a human having an inflamed hip, knee, toe, finger, ankle, elbow, wrist, shoulder, sacro-iliac and/or spinal facet joint.

Veterinary uses are also encompassed within the scope of the invention. For example, HSAs can be administered as described herein, to an animal, such as a mammal, for example a dog or a cat.

For the purposes of the present invention "Transcapsular administration" includes, but is not limited to:
    a) injecting a formulation into the capsule of a degenerating joint,
    b) providing the formulation in a patch attached to the outer wall of the capsule,
    c) providing the formulation in a depot at a location outside but closely closely adjacent to the outer wall of the capsule,
    d) providing the formulation in a depot at a location within at least one of the adjacent bony bodies (hereinafter, "trans-endplate administration"), and
    e) providing the formulation in a depot at a location inside the capsule or within the capsular wall.

As each of the hip, knee, shoulder, ankle, elbow, wrist, toe, finger, sacro-iliac and spinal facet joints may become inflamed due to wear and the presence of pro-inflammatory molecules, the present invention may be beneficially directed to any or all of these joints. In general, each of these joints comprises:
    a) opposing bones having respective opposing hyaline cartilage articular surfaces,
    b) a peripheral, collagenous ligamentous capsule connecting the articular surfaces and defining a central joint space,
    c) a synovium lining upon an inner wall of the capsule, and
    d) synovial fluid contained within the joint space.

In some preferred embodiments, the target joint is a spinal facet joint. The spinal facet joint capsule may contribute to back or leg pain in at least one of the following ways:
    a) chemical sensitization of nerve fibrils contained within the collagenous ligaments of the spinal facet joint capsule,
    b) mediation of and/or direct degeneration of the hyaline articular surfaces, and/or
    c) chemical sensitization of nerve fibrils adjacent or in proximity to a facet joint due to exudation of inflammatory molecules from the capsule during mechanical capsular hydraulic pumping.

Accordingly, the present inventors believe that intra-capsular administration of HSAs may therapeutically benefit the spinal facet joint capsule by i) preventing cytokine binding to the nerve fibrils within the ligament portion of the spinal facet joint capsule, ii) preventing further degradation of the hyaline cartilage portion of the spinal facet joint, and/or iii) preventing cytokine binding to the extra-capsular nerve fibrils.

The present invention is directed to providing directly into an inflamed joint at least one highly specific antagonist capable of specifically inhibiting pro-inflammatory processes in the joint. Preferably, the HSA specifically inhibits the action of a pro-inflammatory molecule released by local hyaline cartilage cells, local synovial cells or invading macrophages during the degenerative joint process.

In some embodiments, the antagonist is capable of specifically inhibiting a pro-inflammatory cytokine selected from the group consisting of TNF-α, an interleukin (preferably, IL-1β, Il-6 and IL-8), FAS, an FAS ligand, and IFN-gamma. Some of these specific inhibitors include those identified on pages 5-18 of U.S. Published Patent Application U.S. Published Patent Application No. US 2003/0039651 ("Olmarker II"), the specification of which is incorporated by reference in its entirety.

In some embodiments, the HSA inhibits the pro-inflammatory molecule by preventing its production. In some embodiments, the HSA inhibits the pro-inflammatory molecule by binding to a membrane-bound pro-inflammatory molecule. In others, the HSA inhibits the pro-inflammatory molecule by binding to a solubilized, e.g., soluble, pro-inflammatory molecule. In some embodiments, the HSA inhibitor inhibits the pro-inflammatory molecule by both binding to membrane bound pro-inflammatory molecules and to solubilized pro-inflammatory molecules. In some embodiments, the HSA is a monoclonal antibody ("mAb"). The use of mAbs is highly desirable since they bind specifically to a certain target protein and to no other proteins. In some embodiments, the HSA inhibits the pro-inflammatory molecule by binding to a natural receptor of the target pro-inflammatory molecule. In some embodiments, the pro-inflammatory molecule is a pro-inflammatory cytokine.

In some embodiments, the HSA is a highly specific TNF-α inhibitor. In some embodiments, the TNF-α inhibitor neutralizes the activity of the TNF-α by binding to membrane bound TNF-α. In some embodiments, the TNF-α inhibitor neutralizes the activity of TNF-α by both binding to membrane bound TNF-α and to soluble TNF-α. In some embodiments, the HSA inhibits the cytokine by binding to a natural receptor of TNF-α. In some embodiments, the TNF-α inhibitor is an inhibitor of TNF-α synthesis.

Preferred TNF-α antagonists include, but are not limited to, the following: infliximab (REMICADE®(infliximab), -Johnson and Johnson); D2E7, a human anti-TNF monoclonal antibody (Knoll Pharmaceuticals, Abbott Laboratories); CDP 571 (a humanized anti-TNF IgG4 antibody); CDP 870 (an anti-TNF alpha humanized monoclonal antibody fragment), both from Celltech; and onercept, a recombinant TNF binding protein (r-TBP-1) (Serono).

TNF antagonists suitable for compositions, combination therapy, co-administration, devices and/or methods of the present invention (optionally further comprising at least one antibody, specified portion and variant thereof, of the present invention), include, but are not limited to, anti-TNF antibodies (e.g., at least one TNF antagonist (e.g., but not limited to a TNF chemical or protein antagonist, TNF monoclonal or polyclonal antibody or fragment, a soluble TNF receptor (e.g., p55, p70 or p85) or fragment, fusion polypeptides thereof, or a small molecule TNF antagonist, e.g., TNF binding protein I or II (TBP-1 or TBP-II), nerelimonmab, infliximab, adalimumab (HUMIRA®), CDP-571, CDP-870, afelimomab, lenercept, and the like), antigen-binding fragments thereof, and receptor molecules which bind specifically to TNF; compounds which prevent and/or inhibit TNF synthesis, TNF release or its action on target cells, such as thalidomide, tenidap, phosphodiesterase inhibitors (e.g, pentoxifylline and rolipram), A2b adenosine receptor agonists and A2b adenosine receptor enhancers; compounds which prevent and/or inhibit TNF receptor signalling, such as mitogen activated protein (MAP) kinase inhibitors; compounds which block and/or inhibit membrane TNF cleavage, such as metalloproteinase inhibitors; compounds which block and/or inhibit TNF activity, such as angiotensin converting enzyme (ACE) inhibitors (e.g., captopril); and compounds which block and/or inhibit TNF production and/or synthesis, such as MAP kinase inhibitors.

As used herein, a "tumor necrosis factor antibody," "TNF antibody," "TNFα antibody," or fragment and the like decreases, blocks, inhibits, abrogates or interferes with TNFα activity in vitro, in situ and/or preferably in vivo. For example, a suitable TNF human antibody of the present invention can bind TNFα and includes anti-TNF antibodies, antigen-binding fragments thereof, and specified mutants or domains thereof that bind specifically to TNFα. A suitable TNF antibody or fragment can also decrease block, abrogate, interfere, prevent and/or inhibit TNF RNA, DNA or protein synthesis, TNF release, TNF receptor signaling, membrane TNF cleavage, TNF activity, TNF production and/or synthesis.

Chimeric antibody cA2 consists of the antigen binding variable region of the high-specificity neutralizing mouse anti-human TNFα IgG1 antibody, designated A2, and the constant regions of a human IgG1, kappa immunoglobulin. The human IgG1 Fc region improves allogeneic antibody effector function, increases the circulating serum half-life and decreases the immunogenicity of the antibody. The avidity and epitope specificity of the chimeric antibody cA2 is derived from the variable region of the murine antibody A2. In a particular embodiment, a preferred source for nucleic acids encoding the variable region of the murine antibody A2 is the A2 hybridoma cell line.

Chimeric A2 (cA2) neutralizes the cytotoxic effect of both natural and recombinant human TNFα in a dose dependent manner. From binding assays of chimeric antibody cA2 and recombinant human TNFα, the specificity constant of chimeric antibody cA2 was calculated to be $1.04 \times 10^{10} M^{-1}$. Preferred methods for determining monoclonal antibody specificity and specificity by competitive inhibition can be found in Harlow, et al., *antibodies: A Laboratory Manual*, Cold Spring Harbor Laboratory Press, Cold Spring Harbor, N.Y. (1988); Colligan et al., eds., *Current Protocols in Immunology*, Greene Publishing Assoc. and Wiley Interscience, New York, (1992-2000); Kozbor et al., *Immunol. Today*, 4:72-79 (1983); Ausubel et al., eds. *Current Protocols in Molecular Biology*, Wiley Interscience, New York (1987-2000); and Muller, *Meth. Enzymol.*, 92:589-601 (1983), which references are entirely incorporated herein by reference.

In a particular embodiment, murine monoclonal antibody A2 is produced by a cell line designated c134A. Chimeric antibody cA2 is produced by a cell line designated c168A.

Additional examples of monoclonal anti-TNF antibodies that can be used in the present invention are described in the art (see, e.g., U.S. Pat. No. 5,231,024; Möller, A. et al., *Cytokine* 2(3):162-169 (1990); U.S. application Ser. No. 07/943, 852 (filed Sep. 11, 1992); Rathjen et al., International Publication No. WO 91/02078 (published Feb. 21, 1991); Rubin et al., EPO Patent Publication No. 0 218 868 (published Apr. 22, 1987); Yone et al., EPO Patent Publication No. 0 288 088 (Oct. 26, 1988); Liang, et al., *Biochem. Biophys. Res. Comm.* 137:847-854 (1986); Meager, et al., *Hybridoma* 6:305-311 (1987); Fendly et al., *Hybridoma* 6:359-369 (1987); Bringman, et al., *Hybridoma* 6:489-507 (1987); and Hirai, et al., *J. Immunol. Meth.* 96:57-62 (1987), which references are entirely incorporated herein by reference).

Preferred TNF receptor molecules useful in the present invention are those that bind TNFα with high specificity (see, e.g., Feldmann et al., International Publication No. WO 92/07076 (published Apr. 30, 1992); Schall et al., *Cell* 61:361-370 (1990); and Loetscher et al., *Cell* 61:351-359 (1990), which references are entirely incorporated herein by reference) and optionally possess low immunogenicity. In particular, the 55 kDa (p55 TNF-R) and the 75 kDa (p75 TNF-R) TNF cell surface receptors are useful in the present invention. Truncated forms of these receptors, comprising the extracellular domains (ECD) of the receptors or functional portions thereof (see, e.g., Corcoran et al., *Eur. J. Biochem.* 223:831-840 (1994)), are also useful in the present invention. Truncated forms of the TNF receptors, comprising the ECD, have been detected in urine and serum as 30 kDa and 40 kDa TNFα: inhibitory binding proteins (Engelmann, H. et al., *J. Biol. Chem.* 265:1531-1536 (1990)). TNF receptor multimeric molecules and TNF immunoreceptor fusion molecules, and derivatives and fragments or portions thereof, are additional examples of TNF receptor molecules which are useful in the methods and compositions of the present invention. The TNF receptor molecules which can be used in the invention are characterized by their ability to treat patients for extended periods with good to excellent alleviation of symptoms and low toxicity. Low immunogenicity and/or high specificity, as well as other undefined properties, can contribute to the therapeutic results achieved.

TNF receptor multimeric molecules useful in the present invention comprise all or a functional portion of the ECD of two or more TNF receptors linked via one or more polypeptide linkers or other nonpeptide linkers, such as polyethylene glycol (PEG). The multimeric molecules can further comprise a signal peptide of a secreted protein to direct expression of the multimeric molecule. These multimeric molecules and methods for their production have been described in U.S. application Ser. No. 08/437,533 (filed May 9, 1995), the content of which is entirely incorporated herein by reference.

TNF immunoreceptor fusion molecules useful in the methods and compositions of the present invention comprise at least one portion of one or more immunoglobulin molecules and all or a functional portion of one or more TNF receptors. These immunoreceptor fusion molecules can be assembled as monomers, or hetero- or homo-multimers. The immunoreceptor fusion molecules can also be monovalent or multivalent. An example of such a TNF immunoreceptor fusion molecule is TNF receptor/IgG fusion protein. TNF immunoreceptor fusion molecules and methods for their production have been described in the art (Lesslauer et al., *Eur. J. Immunol.* 21:2883-2886 (1991); Ashkenazi et al., *Proc. Natl. Acad. Sci. USA* 88:10535-10539 (1991); Peppel et al., *J. Exp. Med.* 174:1483-1489 (1991); Kolls et al., *Proc. Natl. Acad. Sci. USA* 91:215-219 (1994); Butler et al., *Cytokine* 6(6):616-623 (1994); Baker et al., *Eur. J. Immunol.* 24:2040-2048 (1994); Beutler et al., U.S. Pat. No. 5,447,851; and U.S. application Ser. No. 08/442,133 (filed May 16, 1995), each of which references are entirely incorporated herein by reference). Methods for producing immunoreceptor fusion molecules can also be found in Capon et al., U.S. Pat. No. 5,116, 964; Capon et al., U.S. Pat. No. 5,225,538; and Capon et al., *Nature* 337:525-531 (1989), which references are entirely incorporated herein by reference.

A functional equivalent, derivative, fragment or region of a TNF receptor molecule refers to the portion of the TNF receptor molecule, or the portion of the TNF receptor molecule sequence which encodes the TNF receptor molecule, that is of sufficient size and sequences to functionally resemble TNF receptor molecules that can be used in the present invention (e.g., bind TNFα with high specificity and possess low immunogenicity). A functional equivalent of a TNF receptor molecule also includes modified TNF receptor molecules that functionally resemble TNF receptor molecules that can be used in the present invention (e.g., bind TNFα with high specificity and possess low immunogenicity). For example, a functional equivalent of a TNF receptor molecule can contain a "SILENT" codon or one or more amino acid substitutions, deletions or additions (e.g., substitution of one acidic amino acid for another acidic amino acid; or substitution of one codon encoding the same or different hydrophobic amino acid for another codon encoding a hydrophobic amino acid). See Ausubel et al., *Current Protocols in Molecular Biology*, Greene Publishing Assoc. and Wiley-Interscience, New York (1987-2003).

In some embodiments, the monoclonal antibody that inhibits TNF-α is selected from the group consisting of monoclonal rodent-human antibodies, rodent antibodies, human antibodies or any portions thereof, having at least one antigen binding region of an immunoglobulin variable region, which antibody binds TNF-α. Preferably, this monoclonal antibody is selected from the group of compounds disclosed in U.S. Pat. No. 6,277,969, the specification of which is entirely incorporated by reference. In some embodiments, the infliximab is delivered in a formulation having an infliximab concentration of between 30 mg/ml and 60 mg/ml. Preferably, it is provided to produce a concentration in the target capsule of 1 to 20 ug/ml.

In one embodiment, a cytokine antagonist, e.g., a TNF-α antagonist, such as REMICADE® infliximab or Etanercept is delivered to the sacro-iliac joint.

In one embodiment, an HSA (such as a TNF-α antagonist, e.g. REMICADE® infliximab or Etanercept), can be administered to inhibit or prevent sacroiliitis of the sacro-iliac joint or the advance of ankylosing spondylitis (AS) and other, e.g., related, spondylarthropies (SpA), or alleviate their symptoms, e.g., inflammation and subsequent fibrous and bony ankylosis. With regard to anklyosing spondylitis, the inflammation starts outside the capsule at the junction of the tendon and bone. In one embodiment, administration of the HSA, e.g., TNF-α antagonist, is local, for example, administration at the junction of the tendon and the bone or transcapsular administration.

In some embodiments, the HSA is a specific antagonist of a pro-inflammatory interleukin. Preferably, the target interleukin is selected from the group consisting IL-1β, IL-2, IL-6 and IL-8, IL-12 and IL-19. Preferred antagonists include but are not limited to Kineretg (recombinant IL 1-RA, Amgen), IL1-Receptor Type 2 (Amgen) and IL-1 Trap (Regeneron).

In some embodiments, the highly specific antagonist is an inhibitor of p38 MAP kinase, preferably, a small molecule inhibitor of p38 MAP kinase. The inhibition of p38 MAP kinase is believed to block production of both TNF-α and Il-2, both of which are pro-inflammatory cytokines. The small molecule inhibitors of p38 MAP kinase are very specific and potent (~nM). Without wishing to be tied to a theory, it is believed that inhibition of p38 should not block TGF signaling nor TGF activity. It is further believed that p38 inhibitors may also block induction of some metalloproteinases, COX 2 and NO synthetase. It is further believed that P38 inhibitors do not inhibit interleukins involved in immune cell proliferation such as IL-2. Preferably, it is provided in a 10 nM to 10 uM dose. Some high specificity antagonists of p 38 kinase are disclosed in Zhang, *J. Biol. Chem.*, 272(20):13397-402 (May 16, 1997); Pargellis, *Nature Structural Biology*, 9(4):268-272 (April 2002), and Chae, *Bone*, 28(1):45-53 (January 2001), and in U.S. Pat. Nos. 6,541,477 ("Goehring") and U.S. Pat. No. 5,965,583 (Beers), the specifications of which is hereby incorporated by reference in its entirety. Preferably, the HSA of p38 kinase is administered in a dosage to produce a local tissue concentration of between about 5 ug/kg and 50 ug/kg.

In some embodiments, the highly specific antagonist is a p38 kinase inhibitor selected from the group consisting of:
a) diaryl imidizole;
b) N,N'-diaryl urea (developed by Bayer, Boehringer Ingelheim and Vertex);
c) N,N-diaryl urea (developed by Vertex);
d) Benzophenone (developed by Leo Pharmaceuticals);
e) Pyrazole ketone (developed by Hoffman-LaRoche);
f) Indole amide (developed by GlaxoSmithKliine and Scios);
g) Diamides (developed by AstraZeneca);
h) Quinazoline (developed by GlaxoSmithKline);
i) Pyrimido [4,5-d]pyrimidinone (developed by GlaxoSmithKline and Hoffman LaRoche); and
j) Pyridylamino-quinazolines (developed by Scios).

In some embodiments, the highly specific antagonist is a p38 kinase inhibitor selected from the group consisting of:
a) SK&F 86002;
b) SB 203580;
c) L-167307;
d) HEP 689;
e) SB220025;
f) VX-745;

g) SU4984;
h) RWJ 68354;
i) ZM336372;
j) PD098059;
k) SB235699; and
l) SB220025.

Members of this group are described, for example, in Zhang et al., supra, Pargellis et al., supra, Chae, supra, Cirillo et al., *Current Topics in Medicinal Chemistry*, 2, 1021-1035 (2002), Boehm et al., *Exp. Opin. Ther. Patents*, 10(1):25-38 (2000), and Lee et al., *Immunopharmacology*, 47: 185-2001 (2000).

In some embodiments, the highly specific antagonist is a p38 kinase inhibitor characterized as a 1-aryl-2-pyridinyl heterocycle. In some embodiments, the 1-aryl-2-pyridinyl heterocycle is selected from the group consisting of:
 a) 4,5 substituted imidazole,
 b) 1,4,5 substitutued imidizole;
 c) 2,4,5 substitutued imidizole;
 d) 1,2,4,5 substituted imidizole; and
 e) non-imidizole 5-membered ring heterocycle.

In some embodiments, the highly specific antagonist is a p38 kinase inhibitor having at least 3 cyclic groups.

In some embodiments, the highly specific antagonist is a p38 kinase inhibitor selected from the group consisting of a molecule that is readily soluble in water and a substantially water insoluble molecule. In some embodiments, the highly specific antagonist is a p38 kinase inhibitor that is a substantially water insoluble molecule.

The present inventors note that degenerative joint disease ("DJD") involves the progressive degeneration of a joint in which many factors are involved. In many of these instances, simply providing a single dose or even a regimen over the space of a few days may not be sufficient to resolve the DJD. For example, if DJD were caused in part by mechanical instability or wear in the joint, then simply providing a one-time therapy for the joint cells and fibrils will likely only delay the onset of the DJD. Therefore, there is a need to provide a long-term drug therapy treatment of DJD that does not require multiple injections.

Because it is believed that the target molecules of interest may both produce pain and degrade the joint when present within the capsule, it is desirable for the HSA to remain within the joint as long as possible in a pharmaceutically effective amount. The half-life of the HSA within the joint will depend upon many factors, including the size of the HSA and its charge. In general, the larger the molecular weight of the HSA, the more likely it is to remain contained by the capsule portion of the joint.

When using an HSA whose half-life is relatively short, it would be desirable for a relatively large dose of the HSA to be administered into the joint. In this condition, quick depletion of the HSA would not cause the HSA to fall below therapeutically effective levels until an extended period.

Although a large dose of the HSA would be desirable in such instances, it is also known that nociceptors present within the inner wall of the capsule react to increased pressure and produce pain, and that one avenue for increasing the pressure in the capsule is to inject a critical volume of water. In some cases, and in the relatively small spinal facet joint in particular, an added amount of as little as a few cc's by volume could produce pain. Accordingly, if a dilute concentration of an HSA is added to the synovial fluid to provide a large dose, the resulting pressure increase caused by this added volume could be sufficient to cause acute pain.

For example, if it were determined that 100 mg of an HSA was needed to therapeutically affect a joint, and that HSA was provided in concentrations of 30-60 mg/ml, then at least 1.5 ml of the HSA would need to be injected into the capsule in order to provide the desired therapeutic effect. However, when injecting volumes into the capsule, and in particular a spinal facet joint capsule, it is desirable that the volume of drug delivered be no more than 1 ml, preferably no more than 0.5 ml, more preferably between 0.1 and 0.3 ml. When injected in these smaller quantities, it is believed the added volume will not cause an appreciable pressure increase in the capsule.

Accordingly, in some embodiments, the concentration of the HSA (preferably, the p38 kinase or TNF-α antagonist) in the administered drug is at least 100 mg/ml. In this condition, no more than 1 ml of the drug need be injected. Preferably, the concentration of the TNF-α antagonist in the administered drug is at least 200 mg/ml. In this condition, no more than 0.5 ml of the drug need be injected. Preferably, the concentration of the TNF-α antagonist in the administered drug is at least 500 mg/ml. In this condition, between 0.1 and 0.3 ml of the drug need be injected.

In some preferred embodiments, the HSA is combined in the formulation with a viscosupplement. The viscosupplement has a viscosity and elasticity substantially similar to that of natural healthy synovial fluid.

Preferably, the viscosupplement comprises glycosaminoglycans (GAGS). GAGS are biopolymers consisting of repeating polysaccharide units, and are present in nature on the cell surface as well as in the extracellular matrix of animals. GAGS are long unbranched polysaccharides containing a repeating disaccharide unit. The disaccharide unit contains either of two modified sugars, N-acetylgalactosamine or N-acetylglucosamine and a uronic acid such as glucuronate or iduronate. GAGS are highly negatively charged molecules, with extended conformation that imparts high viscosity to the solution. In addition to high viscosity, GAGS routinely possess low compressability, which makes these molecules ideal for a lubricating fluid in the joints. At the same time, their rigidity provides structural integrity to cells and provides passageways between cells, allowing for cell migration.

Hyaluronic acid (HA) is a high molecular weight polysaccharide of N-acetyl glucosamine and glucuronic acid molecules that is naturally occurring in all mammals in a variety of tissue and some bacterial species. For the purposes of this invention, HA includes any derivatives such as hyaluronan and hyaluronic acid itself with H+ion attached to the COO⁻ group, and salts of hyaluronic acid whereby another positive ion replaces the H+ ion, as for example, with $Na^+$ which forms sodium hyaluronate. Also included in the definition of HA is any physically or chemically cross-linked hyaluronic acid or derivative. HA is unique among the GAGS in that it does not contain any sulphate and is not found covalently attached to proteins as a proteoglycan. HA polymers are very large with molecular weights of between about 100,000 and 10,000,000 and can displace a large volume of water. For the purposes of the present invention, a preferred embodiment includes a non-cross linked HA with a molecular weight of 0.5-10 M Dalton.

Preferably, the viscosupplement is selected from the group consisting of hyaluronic acid and hyaluronate (either cross-linked or uncross-linked).

In some embodiments, the HSA is provided in a sustained release device (or "sustained delivery device"). The sustained release device is adapted to remain within the joint for a prolonged period and slowly release the HSA contained therein to the surrounding environment. This mode of delivery allows an HSA to remain in therapeutically effective amounts within the joint for a prolonged period.

Preferably, the sustained release device comprises a bioresorbable material whose gradual erosion causes the gradual release of the HSA to the joint environment. In some embodiments, the sustained release device comprises a bioresorbable polymer. Preferably, the bioresorbable polymer has a half-life of at least one month, more preferably at least two months, more preferably at least 6 months. In some embodiments, the sustained release device comprises GAGS.

In some embodiments, the sustained release device provides controlled release. In others, it provides continuous release. In others, it provides intermittent release. In others, the sustained release device comprises a biosensor.

In some embodiments, the sustained delivery device comprises bioerodable macrospheres. The HSA is preferably contained in a gelatin (or water or other solvent) within the macrosphere, and is released to the joint environment when the outer shell has been eroded. The device can include a plurality of macrospheres having outer shells of varying thickness, so that the sequential breakdown of the outer shells provides periodic release of the HSA.

In some embodiments, the sustained delivery device comprises an inflammatory-responsive delivery system, preferably comprising bioerodable microspheres that are eroded by invading macrophages. This technology provides a high correspondence between physiologic inflammation of disc environment and the release of the HSAs into that environment. Preferably, the technology disclosed in Brown et al., *Arthritis. Rheum.*, 41(12):2185-95 (December 1998) is selected.

In some embodiments, the sustained delivery device comprises a device disclosed in U.S. Pat. No. 5,728,396 ("Peery"), the specification of which is incorporated by reference in its entirety.

In some embodiments, the sustained delivery device comprises a liposomal delivery system, such as that disclosed in WO 03/000190. Liposomes are small spheres whose walls are layers of lipids with water. As they form, liposomes entrap water and any water soluble solutes that are present. Because of this entrapping ability, they are useful as delivery systems. For the purposes of the present invention, a preferred embodiment includes the use of a multilamellar vesicle, and any naturally occurring phospholipid, such as dipalmitoylphosphatidylcholine (DPPC).

A liposome may be a vesicle having at least one lipid bilayer surrounding an inner liquid phase (a lipid bilayer surrounding either a liquid core or a liquid phase dispersed between it and another lipid bilayer). The liposome may have various structures such as multilamellar (MLVs), unilamellar (ULVs) and paucilamellar (PLVs) vesicles. The resulting structure of the liposome is dependent, in part, on the choice of materials forming the hydrophobic phase and the manufacturing parameters, such as temperature and incubation time.

Some liposomes comprise at least one amphiphilic bilayer-forming substance. The therapeutic substances contained therein may be contained either within the lipid bilayer or the hydrophilic compartments of the liposome. The amphiphilic bilayer-forming substance comprises both a hydrophilic and a lipophilic group and is capable of forming, either alone or in combination with other lipids, the bilayer of a liposome. The lipid can have single or multiple lipophilic side chains being either saturated or unsaturated in nature and branched or linear in structure. The amphiphilic bilayer-forming substance can be a phosphoholipid or a ceramide.

In some embodiments, the sustained delivery device comprises a plurality (preferably at least one hundred) of water-containing chambers, each chamber containing the HSA. Each chamber is defined by bilayer lipid membranes comprising synthetic duplicates of naturally occurring lipids. The release of the drug can be controlled by varying at least one of the aqueous excipients, the lipid components, and the manufacturing parameters. Preferably, the formulation comprises no more than 10% lipid. In some embodiments, the DEPOFOAM™ technology of Skyepharma PLC (located in London, United Kingdom) is selected.

In some embodiments, the sustained delivery device comprises a delivery system disclosed in U.S. Pat. No. 5,270,300 ("Hunziker"), the specification of which is incorporated by reference in its entirety.

In some embodiments, the sustained delivery device comprises the co-polymer poly-DL-lactide-co-glycolide (PLG). Preferably, the formulation is manufactured by combining the HSA, the co-polymer and a solvent to form a droplet, and then evaporating the solvent to form a microsphere. The plurality of microspheres are then combined in a biocompatible diluent. Preferably, the HSA is released from the co-polymer by its diffusion therethrough and by the biodegradation of the co-polymer. In some embodiments hereof, the ProLease™ technology of Alkermes (located in Cambridge, Mass.) is selected.

Hydrogels can also be used as a sustained release device to deliver the HSA in a time-release manner to the joint environment. A "hydrogel" is a substance formed when an organic polymer (natural or synthetic) is set or solidified to create a three-dimensional open-lattice structure that entraps molecules of water or other solution to form a gel. The solidification can occur, e.g., by aggregation, coagulation, hydrophobic interactions, or cross-linking. The hydrogels employed in this invention rapidly solidify to keep the HSA at the application site, thereby eliminating undesired migration from the joint. The hydrogels are also biocompatible, e.g., not toxic, to any cells suspended in the hydrogel.

A "hydrogel-HSA composition" is a suspension of a hydrogel containing desired HSA. The hydrogel-HSA composition forms a uniform distribution of HSA with a well-defined and precisely controllable density. Moreover, the hydrogel can support very large densities of HSA.

Hydrogels suitable for use in the present invention include water-containing gels, i.e., polymers characterized by hydrophilicity and insolubility in water. See, for instance, "Hydrogels", pages 458-459 in *Concise Encyclopedia of Polymer Science and Engineering*, Eds. Mark et al., Wiley and Sons (1990), the disclosure of which is incorporated herein by reference. Although their use is optional in the present invention, the inclusion of hydrogels is highly preferred since they tend to contribute a number of desirable qualities. By virtue of their hydrophilic, water-containing nature, hydrogels can:

a) house viable cells, such as mesenchymal stems cells, and b) assist with load bearing capabilities of the joint.

In a preferred embodiment, the hydrogel is a fine, powdery synthetic hydrogel. Suitable hydrogels exhibit an optimal combination of such properties as compatibility with the matrix polymer of choice, and biocompatibility. The hydrogel can include any of the following: polysaccharides, proteins, polyphosphazenes, poly(oxyethylene)-poly(oxypropylene) block polymers, poly(oxyethylene)-poly(oxypropylene) block polymers of ethylene diamine, poly (acrylic acids), poly(methacrylic acids), copolymers of acrylic acid and methacrylic acid, poly(vinyl acetate), and sulfonated polymers.

In general, these polymers are at least partially soluble in aqueous solutions, e.g., water, or aqueous alcohol solutions that have charged side groups, or a monovalent ionic salt thereof. There are many examples of polymers with acidic side groups that can be reacted with cations, e.g., poly(phosphazenes), poly(acrylic acids), and poly(methacrylic acids). Examples of acidic groups include carboxylic acid groups, sulfonic acid groups, and halogenated (preferably fluorinated) alcohol groups. Examples of polymers with basic side groups that can react with anions are poly(vinyl amines), poly(vinyl pyridine), and poly(vinyl imidazole).

In some embodiments, the sustained delivery device includes a polymer selected from the group consisting of PLA, PGA, PCL, and mixtures thereof.

When using an HSA having a relatively long half-life within the joint, then it may be assumed that a relatively small dose of the HSA can be administered into the joint. In this condition, the slow depletion of the HSA would not cause the HSA to fall below therapeutically effective levels until an extended period of time has elapsed.

In some embodiments in which HSAs have long half-lives within the joint, the dose administered can be very small. (*Shruder*) For example, if it is believed that an HSA is effective when present in the target tissue in the range of 1-10 mg/kg or 1-10 ppm (as is the case for the TNF-α antagonist REMICADE® (infliximab), and since a typical spinal facet joint has a volume of about 3 ml (or 3 cc, or 3 g) of synovial fluid, then only about 3-30 µg of the HSA need be administered to the disc in order to provide a long lasting effective amount of the drug. As a point of reference, Tobinick discloses that at least 1 mg of cytokine antagonist should be administered perispinally in order to cure back pain. The smaller amounts available by this route reduce the chances of deleterious side effects of the HSA.

For example, suppose a clinician administered 0.3 ml of 60 mg/ml infliximab into a 2.7 cc facet joint, thereby producing a infliximab concentration in the joint of about 6 mg/ml, or 6 parts per thousand. Without wishing to be tied to a theory, if infliximab has the same half-life within the synovial fluid of the joint as it does when administered systemically (i.e., about 1 week), then the concentration of infliximab would remain above about 10 ppm for about 9 weeks. Therefore, if another dose were needed, the clinician would only need to provide the second dose after about two months.

Therefore, in some embodiments, the HSA is provided in a dose of less than 1 mg, e.g., in a maximum amount of 0.5 mg, preferably, less than 0.5 mg, more preferably, less than 0.1 mg, more preferably less than 0.01 mg. In one embodiment, a formulation comprising the HSA is administered in a volume of between 0.03 ml and 0.3 ml. The smaller amounts available by this route reduce the chances of deleterious side effects of the HSA. Preferably, the HSA provided in these smaller amounts is a TNF-α antagonist, more preferably it is infliximab.

In preferred embodiments, the formulation of the present invention is administered directly into the joint through the outer wall of the capsule. More preferably, the direct administration includes depositing the HSA in the synovial fluid-containing portion of the joint. In this condition, the fibrous nature of the capsule that surrounds and contains the synovial fluid will help keep the HSA contained within the capsule.

Preferably, the formulation of the present invention is injected into the joint through a small bore needle. More preferably, the needle has a bore diameter of 22 gauge or less, so that the possibilities of producing a rupture are mitigated. More preferably, the needle has a bore of 24 gauge or less, so that the possibilities of producing a rupture are even further mitigated.

If the volume of the direct injection of the formulation is sufficiently high so as to cause a concern of overpressurizing the capsule, then it is preferred that at least a portion of the synovial fluid be removed prior to direct injection. Preferably, the volume of removed synovial fluid is substantially similar to the volume of the formulation to be injected. More preferably, the volume of removed synovial fluid is within 80-120% of the volume of the formulation to be injected.

In other embodiments, the formulation is delivered into the joint space through the cartilage endplate of an adjacent joint bone. This avenue eliminates the need to puncture the capsule, and so eliminates the possibility of its capsule rupture.

In some embodiments, the formulation is administered through a drug pump.

Although the HSAs may therapeutically treat the joint by binding the target pro-inflammatory molecule, and thereby reducing pain and arresting degradation of the ECM, it is believed that at least some of these antagonists do not help repair the damage done by the target molecule to the ECM.

Therefore, there may be a need to provide a therapy that also helps repair the ECM.

In accordance with one aspect of the invention, both the HSA and at least one additional therapeutic agent (for example, a second therapeutic agent) are locally administered into the capsule. Because the HSA is specific, it does not interfere with the locally administered second therapeutic agent, and so each drug may independently work to provide therapy to the diseased joint.

In some embodiments, the HSA and additional therapeutic agent are administered simultaneously. In others, the HSA is administered first. In still others, the additional therapeutic agent is administered first.

Other compounds which may be added intra-capsularly to the joint include, but are not limited to: vitamins and other nutritional supplements; hormones; glycoproteins; fibronectin; peptides and proteins; carbohydrates (both simple and/or complex); proteoglycans; antiangiogenins; antigens; oligonucleotides (sense and/or antisense DNA and/or RNA); BMPs; DBM; antibodies (for example, to infectious agents, tumors, drugs or hormones, inhibitors of soluble TNF-α); and gene therapy reagents. Genetically altered cells and/or other cells may also be included in the matrix of this invention. If desired, substances such as pain killers and narcotics may also be admixed with a polymer for delivery and release to the joint space.

Preferably, healthy cells are introduced into the joint that have the capability of at least partially repairing any damage done to the hyaline articular cartilage or capsule during the degenerative process. In some embodiments, these cells are introduced into the synovial fluid and ultimately produce new extracellular matrix for the hyaline articular cartilage. In others, these cells are introduced into the capsule and produce new extracellular matrix for the capsule.

In some embodiments, these cells are obtained from another human individual (allograft), while in others, the cells are obtained from the same individual (autograft). In some embodiments, the cells are taken from articular hyaline cartilage, while in others, the cells are taken from a non-joint tissue (and may be mesenchymal stem cells). In others, autograft chondrocytes may be used (such as from the hip, knee, shoulder, fingers, or ear).

Preferably, when viable cells are selected as the second agent or therapeutic substance, the viable cells comprise mesenchymal stem cells (MSCs). MSCs provide a special advantage for administration into a degenerating joint because it is believed that they can more readily survive the relatively harsh environment present in the degenerating joint; that they have a desirable level of plasticity; and that they have the ability to proliferate and differentiate into the desired cells.

In some embodiments, the mesenchymal stems cells are obtained from bone marrow, preferably autologous bone marrow. In others, the mesenchymal stems cells are obtained from adipose tissue, preferably autologous adipose tissue.

In some embodiments, the mesenchymal stem cells injected into the joint are provided in an unconcentrated form. In others, they are provided in a concentrated form. When provided in concentrated form, they are preferably uncultured. Uncultured, concentrated MSCs can be readily obtained by centrifugation, filtration, or immuno-absorption. When filtration is selected, the methods disclosed in U.S. Pat. No. 6,049,026 ("Muschler"), the specification of which is incorporated by reference in its entirety, are preferably used. In some preferred embodiments, the matrix used to filter and concentrate the MSCs is also administered into the joint space. If this matrix has suitable lubricating properties, it can be used to restore the lubrication qualities of the joint that were lost during the degradation process.

In some embodiments, cartilage cells (which may be from either an allogeneic or autologous source) or mesenchymal stem cells may be genetically modified to produce a cartilage anabolic agent which could be chosen from the list of growth factors named below. The production of these chondroprotective agents, differentiation promoting agents would lead to tissue repair.

Recent work has shown that plasmid DNA will not elicit an inflammatory response as does the use of viral vectors. Genes encoding cartilage (anabolic) agents such as BMP, etc. may be efficacious if injected into the joint. In addition, overexpression of any of the growth factors listed under growth factor delivery or other agents such as TIMP which would limit local MMP activity would have positive effects on chondrocyte and ECM protection. Preferably, the plasmid contains the genetic code for human TGF-B or EPO.

As used herein, the term "growth factors" encompasses any cellular product that modulates the growth or differentiation of other cells, particularly connective tissue progenitor cells. Preferably, growth factors are delivered after the inhibition of the pro-inflammatory molecules has taken effect. The growth factors that may be used in accordance with the present invention include, but are not limited to, members of the fibroblast growth factor family, including acidic and basic fibroblast growth factor (FGF-1 and FGF-2) and FGF-4, members of the platelet-derived growth factor (PDGF) family, including PDGF-AB, PDGF-BB and PDGF-AA; EGFs; the TGF-β superfamily, including TGF-β1, 2 and 3; osteoid-inducing factor (OIF); angiogenin(s); endothelins; hepatocyte growth factor and keratinocyte growth factor; members of the bone morphogenetic proteins (BMP's) BMP-1, BMP-3, BMP-2; OP-1, BMP-2A, BMP-2B, and BMP-7; HBGF-1 and HBGF-2; growth differentiation factors (GDF's); members of the hedgehog family of proteins, including indian, sonic and desert hedgehog; ADMP-1; other members of the interleukin (IL) family; and members of the colony-stimulating factor (CSF) family, including CSF-1, G-CSF, and GM-CSF, and isoforms thereof; and VEGF.

In some embodiments, the growth factor is selected from the group consisting of TGF-B, bFGF, and IGF-1. These growth factors are believed to promote regeneration of the hyaline articular cartilage. In some embodiments, the growth factor is TGF-B. More preferably, TGF-B is administered in an amount of between 10 ng/ml and 5000 ng/ml, more preferably between 50 ng/ml and 500 ng/ml, more preferably between 100 ng/ml and 300 ng/ml.

In some embodiments, platelet concentrate is provided as an additional therapeutic agent. Preferably, the growth factors released by the platelets are present in an amount at least two-fold (more preferably, four-fold) greater than the amount found in the blood from which the platelets were taken. More preferably, the platelet concentrate is autologous. In some embodiments, the platelet concentrate is platelet rich plasma (PRP). PRP is advantageous because it contains growth factors that can restimulate the growth of the ECM, and because its fibrin matrix provides a suitable scaffold for new tissue growth.

In addition, non-steroidal anti-inflammatory drugs (NSAIDs) may also be selected as additional therapeutic agent. In some embodiments, the NSAID is anabolic, and is preferably selected from the group consisting of TOLMETIN™ (available from Ortho-McNeil), SUPROL™ (available from Johnson & Johnson), and Tiaprofenic acid, (available from Roussel Labs). Preferably, the anabolic NSAID is administered in a dosage sufficient to produce an initial local tissue concentration of between about 5 ug/kg and 500 ug/kg. In some embodiments, the NSAID is a dual inhibitor of both the COX and LOX pathways, and is preferably TEPOXALINTM (available from Johnson & Johnson).

In addition, anti-cathepsins may also be used in accordance with the present invention. It is believed that inhibition of these enzymes inhibits the breakdown of the extracellular matrix. Preferably, the antagonists inhibits a cathepsin selected from the group consisting of cathepsin B, cathepsin L and cathepsin K.

In addition, cycline compounds may also be used as an additional therapeutic agent in accordance with the present invention. Preferably, the cycline compound is administered in an amount effective to inhibit the action of a pro-inflammatory cytokine (such as TNF-α) or MMP. Preferably, the cycline compound is administered in an amount effective to inhibit the action of an MMP released by cells during the degenerative process. More preferably, the cycline compound is administered in an amount effective to both a) inhibit the action of a specific pro-inflammatory cytokine (such as TNF-α), and b) inhibit the action of an ECM-degrading MMP released by cells during the degenerative process.

In some embodiments, the cycline compound is selected from the group of cycline compounds consisting of doxycycline, lymecycline, oxicycline compound, tetracycline, minocycline, chemically modified cycline compound (CMT) and KB-R7785. Preferably, doxycycline is selected.

In some embodiments, anti-inflammatory agents such as an antagonist of PPAR-α.

Since it is known that many pro-inflammatory molecules play a role in joint degeneration, and that the antagonists of the present invention are highly specific, it is further believed that injecting at least two of the highly specific antagonists of the present invention directly into the joint space would be advantageous.

Therefore, in accordance with the present invention, there is provided a method of treating degenerative joint disease, comprising trans-capsularly administering a formulation comprising at least two highly specific antagonists (HSA) selected from the group consisting of:
  i) an inhibitor of a pro-inflammatory interleukin;
  ii) an inhibitor of TNF-α synthesis;
  iii) an inhibitor of membrane-bound TNF-α;
  iv) an inhibitor of a natural receptor of TNF-α;
  v) an inhibitor of NO synthase;
  vi) an inhibitor of PLA$_2$ enzyme;
  vii) an anti-proliferative agent;
  viii) an anti-oxidant;
  ix) an apoptosis inhibitor selected from the group consisting of EPO mimetic peptides, EPO mimetibodies, IGF-I, IGF-II, and caspase inhibitors, and
  x) an inhibitor of MMPs; and
  xi) a p38 kinase inhibitor.

Preferably, at least one of the substances is an antagonist of TNF-α. Preferably, the other substance is an antagonist of an interleukin.

In some embodiments, the formulation comprises a suitable biocompatible carrier such as saline. In some embodiments, the carrier is selected from the carriers disclosed in U.S. Pat. No. 6,277,969 ("Le"), the specification of which is incorporated by reference in its entirety. In some embodiments, the formulation includes a solvent, preferably selected from the group consisting of DMSO and ethanol.

Also in accordance with the present invention, there is provided a formulation for treating degenerative joint disease, comprising:
a) a high specificity antagonist selected from the group consisting of:
   i) an inhibitor of a pro-inflammatory interleukin;
   ii) an inhibitor of TNF-α synthesis;
   iii) an inhibitor of membrane-bound TNF-α;
   iv) an inhibitor of a natural receptor of TNF-α;
   v) an inhibitor of NO synthase;
   vi) an inhibitor of $PLA_2$ enzyme;
   vii) an anti-proliferative agent;
   viii) an anti-oxidant;
   ix) an apoptosis inhibitor selected from the group consisting of EPO mimetic peptides, EPO mimetibodies, IGF-I, IGF-II, and caspase inhibitors;
   x) an inhibitor of MMPs; and
   xi) a p38 kinase inhibitor; and
b) a second therapeutic agent selected from the group consisting of:
   i) a growth factor
   ii) viable cells, and
   iii.) plasmid DNA.

In some embodiments of this formulation, the high specificity antagonist is selected from the group consisting of antagonists of TNF and antagonists of an interleukin.

Because the causes of joint pain may be myriad, and because of the significant cost of many of these specialized HSAs, it would be useful for the clinician to first perform a diagnostic test in order to confirm that the targeted joint in fact possesses high levels of the targeted cytokine prior to providing the injection.

In one embodiment, the diagnostic test comprises a non-invasive diagnostic test comprising using an MRI.

Preferably, the clinician would perform an invasive or non-invasive test upon the synovial fluid of the targeted joint in order to confirm the presence of or quantify the level of the pro-inflammatory cytokine.

In one embodiment, the diagnostic test comprises an invasive test in which a portion of the joint is removed and analyzed. In some embodiments, the clinician removes a portion of the synovial fluid. In others, the clinician removes a portion of the capsule. Preferably, the removed material is a portion of the synovial fluid. The presence of pro-inflammatory cytokines in the removed material may detected by procedures including but not limited to electrophoresis, or an enzyme-linked immunoabsorbent assay (as per Burke, *Br. JBJS,* 84-B (2) (2002). In some embodiments, the invasive test may be performed during arthroscopy.

In some embodiments, the diagnostic methods disclosed in U.S. Pat. No. 6,277,969 ("Le"), the specification of which is incorporated by reference in its entirety, are selected. In these methods, high specificity anti-TNF-α compounds are used as diagnostic tools for detecting TNF-α in the patient known or suspected to have a high level of TNF-α.

In some embodiments, a bioMEMS device containing a "lab on a chip" used in the diagnostic test.

In another embodiment, the diagnostic test comprises evaluating the genetic makeup of the patient and forecasting whether that patient will have a degenerative joint in the future.

After determining the levels of the different pro-inflammatory cytokine in the degenerating joint, the clinician will preferably proceed to compare these diagnosed levels against pre-determined levels of the pro-inflammatory cytokines. If the diagnosed level of the pro-inflammatory cytokine exceeds the pre-determined level, then the clinician may conclude that these higher levels are causing unwanted inflammatory action and proceed to directly inject a specific HSA into the joint capable of inhibiting the targeted protein.

In some embodiments, the predetermined level for an interleukin is 10 pg/ml. In some embodiments, the predetermined level for IL-6 is 10 pg/ml. In other embodiments, the predetermined level for IL-6 is at least 100 pg/ml, e.g., at least 250 pg/ml. In some embodiments, the predetermined level for IL-8 is 10 pg/ml. In other embodiments, the predetermined level for IL-8 is at least 500 pg/ml. In some embodiments, the predetermined level for non-cytokine PGE2 is 10 pg/ml. In some embodiments, the predetermined level for TNF-α is 10 pg/ml (or, in other embodiments, at least 20 pg/ml, or at least 30 pg/ml). In others, the predetermined level for TNF-α is 1 ng/ml. In others, the predetermined level for TNF-α is 1 ng/joint (or, in other embodiments, at least 1000 pg/joint).

It would also be useful to be able to determine whether directly administering the therapeutic substances of the present invention is, in fact, efficacious. Accordingly, one can measure the level of cytokine remaining in the joint after administration.

It is further believed that the present invention can also be used to prevent degeneration of a joint in a human individual, namely, by following a procedure comprising the steps of:
   a) determining a genetic profile of the individual,
   b) comparing the profile of the individual against a pre-determined genetic profile level of at-risk humans,
   c) determining that the individual is at at-risk patient, and
   d) injecting an antagonist of the pro-inflammatory protein into a joint of the individual.

EXAMPLE I

Saline

This non-limiting prophetic example describes how to transcapsularly administer a formulation comprising a HSA and saline into the synovium of a degenerating joint.

Optionally, the clinician uses a diagnostic test to verify that a particular joint has high levels of a particular pro-inflammatory cytokine.

Next, the clinician provides a local anesthetic (such as 5 ml lidocaine) to the region above the joint of concern to reduce subcutaneous pain.

Next, the clinician punctures the skin of the patient above the joint of concern with a relatively large (e.g., 18-19 gauge) needle having a stylet therein, and advances the needle through subcutaneous fat, ligaments and muscles to the outer edge of the capsule.

In the case of HSA injections, the clinician may aspirate a volume of synovial fluid before injection.

Next, the stylet is removed from the needle.

Next, the clinician receives a syringe having a smaller gauge needle adapted to fit within the larger gauge needle. This needle is typically a 22 or 24 gauge needle. The barrel of the syringe contains the formulation of the present invention.

The formulation contains REMICADE® infliximab, and has an infliximab concentration of between about 30 mg/ml and about 60 mg/ml.

Next, the physician advances the smaller needle co-axially through the larger needle and past the distal end of the larger needle, thereby puncturing the capsule. The smaller needle is then further advanced into the center of the synovium. Finally, the clincian depresses the plunger of the syringe, thereby injecting between about 0.1 and 1 ml of the formulation into the synovial fluid.

EXAMPLE II

Sustained Release

This non-limiting prophetic example is substantially similar to that of Example I, except that the formulation comprises a sustained release device comprising the co-polymer poly-DL-lactide-co-glycolide (PLG). The formulation contains infliximab as the antagonist, and has an infliximab concentration of between about 30 mg/ml and about 60 mg/ml.

EXAMPLE III

Cartilage Impact Model

In order to assess cartilage breakdown by inflammatory mediators and the effect of highly specific antagonists on those mediators, a cartilage impact model was established using a drop tower device to apply a peak compressive stress to a cartilage sample of about 20-30 MPa over an area of about 11-15 $mm^2$. Advantages of this model included its clinical relevance due to its potential to mimic several key parameters of OA such as inflammatory cell mediators (by co-culturing with inflammatory cells), and induction of trauma to create the cartilage damage. For this model, the following in vitro parameters were evaluated:
a) histological scoring,
b) GAG release in the media—a measurement of proteoglycan degradation which indicates cartilage extracellular matrix breakdown,
c) GAG content in the tissues by histological stain,
d) PGE2 levels by Enzyme-linked Immunosorbent Assay (ELISA)—a primary product of arachidonic acid metabolism that is synthesized and released upon cell activation, and whose presence indicates an inflammatory response, and
e) Total Nitric Oxide production—measurement of NO production indicates the presence of inflammatory response or mitogenic stimuli.

What is claimed is:

1. A method of treating an inflamed orthopedic joint, said joint comprising i) opposing hyaline cartilage articular surfaces, ii) a peripheral collagenous capsule defining a central joint space and iii) synovial fluid contained within the joint space, comprising trans-capsularly administering into the joint space a formulation comprising an effective amount of an anti-TNF-α monoclonal antibody or antigen-binding fragment thereof such that the inflamed orthopedic joint is treated, the method further comprising providing a therapeutically effective amount of a Growth Differentiation Factor (GDF) to the joint.
2. The method of claim 1, wherein the joint is a knee joint.
3. The method of claim 1, wherein the joint is a hip joint.
4. The method of claim 1, wherein the joint is a spinal facet joint.
5. The method of claim 1, wherein the formulation further comprises a therapeutically effective amount of at least one growth factor.
6. The method of claim 1, wherein the formulation further comprises a liposomal delivery system.
7. The method of claim 1, wherein the formulation is administered in an amount of less than 1 cc.
8. The method of claim 1, wherein the anti-TNF-α monoclonal antibody or antigen-binding fragment thereof is present in the formulation in an amount of at least 100 mg/ml.
9. The method of claim 1, wherein the formulation is provided with a sustained release device.
10. The method of claim 9, wherein the sustained release device comprises a hydrogel.
11. The method of claim 9, wherein the sustained release device provides controlled release.
12. The method of claim 9, wherein the sustained release device provides continuous release.
13. The method of claim 9, wherein the sustained release device provides intermittent release.
14. The method of claim 9, wherein the sustained release device comprises microspheres having a plurality of degradation rates.
15. The method of claim 9, wherein the sustained release device maintains the administered anti-TNF-α monoclonal antibody or antigen-binding fragment thereof at a therapeutically effective level.
16. The method of claim 1, wherein the formulation is provided closely adjacent to the outer wall of the capsule.
17. The method of claim 1, wherein the anti-TNF-α monoclonal antibody or antigen-binding fragment thereof is present in the formulation in a maximum amount of 0.5 mg.
18. The method of claim 1, wherein the formulation further comprises a growth factor, which is provided by platelet concentrate.
19. The method of claim 1, wherein the anti-TNF-α monoclonal antibody or antigen-binding fragment thereof therapeutically inhibits the production of a cytokine.
20. The method of claim 1, wherein the formulation further comprises viable mesenchymal stem cells.
21. The method of claim 1, wherein the formulation is injected into the synovial fluid.
22. The method of claim 1, wherein the formulation includes a viscosupplement.
23. The method of claim 1, wherein a portion of the synovial fluid is removed prior to administration of the-anti-TNF-α monoclonal antibody or antigen-binding fragment thereof.
24. The method of claim 1, wherein the administration is performed through a needle.
25. The method of claim 1, wherein the formulation is administered through a drug pump.
26. The method of claim 1, wherein the formulation is administered in a volume of between 0.03 ml and 0.3 ml.
27. The method of claim 1, wherein the administration comprises providing the formulation in a patch attached to an outer wall of the capsule.
28. The method of claim 1, wherein the administration comprises providing the formulation in a depot at a location closely adjacent an outer wall of the capsule.
29. The method of claim 1, wherein the administration comprises providing the formulation in a depot at a location closely adjacent to an endplate of an adjacent bony body.
30. The method of claim 1, wherein the anti-TNF-α monoclonal antibody or antigen-binding fragment thereof is predominantly released from the formulation by diffusion of the high specificity antagonist through a sustained delivery device.

31. The method of claim 30, wherein the sustained delivery device is a polymer.

32. The method of claim 1, wherein the anti-TNF-α monoclonal antibody or antigen-binding fragment thereof is predominantly released from the formulation by biodegradation of a sustained delivery device.

33. The method of claim 1, wherein the formulation further comprises BMP-1, BMP-3, BMP-2, OP-1, BMP-2A, BMP-2B, or BMP-7.

34. The method of claim 1, wherein the formulation further comprises TGF-β.

35. The method of claim 1, wherein said anti-TNF-α monoclonal antibody or antigen-binding fragment thereof is adalimumab.

36. The method of claim 1, wherein said anti-TNF-α monoclonal antibody or antigen-binding fragment thereof is CDP-571.

37. The method of claim 1, wherein said anti-TNF-α monoclonal antibody or antigen-binding fragment thereof is CDP-870.

38. A method of treating an inflamed orthopedic joint, said joint comprising i) opposing hyaline cartilage articular surfaces, ii) a peripheral collagenous capsule defining a central joint space and iii) synovial fluid contained within the joint space, comprising trans-capsularly administering into the joint space a formulation comprising an effective amount of infliximab, such that the inflamed orthopedic joint is treated, the method further comprising providing a therapeutically effective amount of a Growth Differentiation Factor (GDF) to the joint.

39. The method of claim 1, wherein the GDF is provided to the joint simultaneously with the TNF-α antibody or antigen binding fragment thereof.

40. The method of claim 39, wherein the GDF is provided in the formulation comprising the TNF-α antibody or antigen binding fragment thereof.

41. The method of claim 1, wherein the GDF is provided to the joint separately from the anti-TNF-α monoclonal antibody or antigen-binding fragment thereof.

42. The method of claim 1, wherein the joint is in a mammalian subject with ankylosing spondylitis.

* * * * *

UNITED STATES PATENT AND TRADEMARK OFFICE
CERTIFICATE OF CORRECTION

| | | |
|---|---|---|
| PATENT NO. | : 8,361,467 B2 | Page 1 of 1 |
| APPLICATION NO. | : 10/630227 | |
| DATED | : January 29, 2013 | |
| INVENTOR(S) | : DiMauro et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1771 days.

Signed and Sealed this
Second Day of December, 2014

Michelle K. Lee
*Deputy Director of the United States Patent and Trademark Office*